(12) United States Patent
Kodandaramaiah et al.

(10) Patent No.: US 12,350,010 B2
(45) Date of Patent: Jul. 8, 2025

(54) SYSTEMS AND METHODS FOR MULTIMODAL NEURAL SENSING

(71) Applicant: REGENTS OF THE UNIVERSITY OF MINNESOTA, Minneapolis, MN (US)

(72) Inventors: Suhasa Kodandaramaiah, Minneapolis, MN (US); Leila Ghanbari, Minneapolis, MN (US); Daniel Sousa Schulman, Minneapolis, MN (US); Michael Cary McAlpine, Minneapolis, MN (US); Sarah Swisher, Minneapolis, MN (US); Preston Donaldson, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1010 days.

(21) Appl. No.: 17/111,942

(22) Filed: Dec. 4, 2020

(65) Prior Publication Data

US 2021/0169334 A1 Jun. 10, 2021

Related U.S. Application Data

(60) Provisional application No. 62/944,137, filed on Dec. 5, 2019.

(51) Int. Cl.
*A61B 5/00* (2006.01)
*A61B 5/145* (2006.01)
(Continued)

(52) U.S. Cl.
CPC .......... *A61B 5/0071* (2013.01); *A61B 5/0035* (2013.01); *A61B 5/14503* (2013.01);
(Continued)

(58) Field of Classification Search
CPC . A61B 5/0071; A61B 5/0035; A61B 5/14503; A61B 5/14546; A61B 5/14553;
(Continued)

(56) References Cited

U.S. PATENT DOCUMENTS 8,099,156 B1 * 1/2012 Schnitzer ............... A61B 1/227
600/478
9,791,683 B2 * 10/2017 Doric ................... A61N 5/0622
(Continued)

OTHER PUBLICATIONS

Castagnola et al., "Biologically Compatible Neural Interface to Safely Couple Nanocoated Electrodes to the Surface of the Brain", 2013 (Year: 2013).*

(Continued)

*Primary Examiner* — Adil Partap S Virk
(74) *Attorney, Agent, or Firm* — QUARLES & BRADY LLP

(57) ABSTRACT

A system and method is provided for imaging and monitoring a tissue, such as a cerebral cortex, of a subject. Access to imaging a tissue, such as cerebral cortex, may be provided by removing a portion of a bone, such as a portion of a skull of the subject. A prosthesis, such as an optically transparent prosthesis, may be used to replace the portion of the skull removed and may be conformed to the same 3D contour of the bone that was removed. A data acquisition system, such as an imaging system, may then be affixed to the skull prosthesis and may be used to acquire image data of the tissue of the subject at high spatial and temporal resolution and without interference from intervening bone material.

33 Claims, 8 Drawing Sheets

(51) Int. Cl.
*A61B 5/1455* (2006.01)
*A61B 5/37* (2021.01)
*A61F 2/28* (2006.01)
*A61F 2/30* (2006.01)

(52) U.S. Cl.
CPC ...... *A61B 5/14546* (2013.01); *A61B 5/14553* (2013.01); *A61B 5/37* (2021.01); *A61B 5/6847* (2013.01); *A61F 2/2875* (2013.01); *A61B 5/0042* (2013.01); *A61B 2562/046* (2013.01); *A61F 2002/3009* (2013.01); *A61F 2002/30985* (2013.01)

(58) Field of Classification Search
CPC ....... A61B 5/37; A61B 5/6847; A61B 5/0042; A61B 2562/046; A61B 5/6879; A61F 2/2875; A61F 2002/3009; A61F 2002/30985; A61F 2002/30948; A61F 2/30942
See application file for complete search history.

(56) References Cited

U.S. PATENT DOCUMENTS

| | | | | |
|---|---|---|---|---|
| 9,846,300 | B2* | 12/2017 | Doric | G02B 21/361 |
| 10,791,946 | B2 | 10/2020 | Kuzum | |
| 11,497,401 | B2* | 11/2022 | Tandon | A61B 5/0042 |
| 11,497,576 | B2* | 11/2022 | Kells | A61B 17/3403 |
| 11,867,892 | B2* | 1/2024 | Pathak | A61B 5/002 |
| 2001/0025148 | A1* | 9/2001 | Reischl | A61B 5/121 600/559 |
| 2004/0030258 | A1 | 2/2004 | Williams | A61B 5/4076 600/544 |
| 2004/0064052 | A1* | 4/2004 | Chance | A61B 5/14553 600/476 |
| 2004/0106856 | A1* | 6/2004 | Kimura | A61B 5/0062 250/341.1 |
| 2005/0107716 | A1* | 5/2005 | Eaton | A61B 5/0073 128/903 |
| 2006/0100526 | A1* | 5/2006 | Yamamoto | A61B 5/743 600/476 |
| 2006/0122477 | A1* | 6/2006 | Hirabayashi | A61B 5/14553 600/344 |
| 2009/0005711 | A1* | 1/2009 | Konofagou | A61M 37/0092 601/2 |
| 2010/0309547 | A1* | 12/2010 | Hirata | G01N 21/01 359/382 |
| 2011/0237921 | A1* | 9/2011 | Askin, III | A61B 5/24 607/116 |
| 2012/0123236 | A1* | 5/2012 | Boularot | A61B 90/11 600/378 |
| 2012/0230566 | A1* | 9/2012 | Dean | G06T 15/00 382/128 |
| 2013/0046229 | A1* | 2/2013 | Konofagou | A61B 5/0071 604/22 |
| 2013/0110252 | A1* | 5/2013 | Bake | A61F 2/30756 623/23.57 |
| 2013/0304216 | A1* | 11/2013 | Paspa | A61N 1/0539 623/17.19 |
| 2014/0005492 | A1* | 1/2014 | Harttig | A61B 5/14735 156/60 |
| 2014/0257518 | A1* | 9/2014 | McAlpine | A61L 27/54 428/17 |
| 2015/0088224 | A1* | 3/2015 | Goldwasser | A61N 1/36025 607/45 |
| 2016/0007874 | A1* | 1/2016 | Ma | A61B 5/6868 600/377 |
| 2016/0058316 | A1* | 3/2016 | Vitale | A61N 1/0534 156/60 |
| 2016/0296312 | A1* | 10/2016 | Kuhn | A61B 5/6868 |
| 2017/0128015 | A1* | 5/2017 | Rogers | A61B 5/291 |
| 2017/0199364 | A1* | 7/2017 | Doric | G02B 21/0008 |
| 2017/0363849 | A1* | 12/2017 | Doric | G02B 27/141 |
| 2018/0178013 | A1* | 6/2018 | Bouton | A61N 1/0534 |
| 2018/0360366 | A1* | 12/2018 | Gayl | A61F 2/2875 |
| 2019/0090801 | A1* | 3/2019 | Rogers | A61B 5/4836 |
| 2019/0380585 | A1* | 12/2019 | Chen | G02B 21/0048 |
| 2019/0381314 | A1* | 12/2019 | Howard | A61B 5/0071 |
| 2020/0093474 | A1* | 3/2020 | Macknik | A61B 17/0218 |
| 2020/0405204 | A1* | 12/2020 | Howard | A61B 5/14546 |
| 2021/0059578 | A1* | 3/2021 | Nassi | A61K 49/005 |
| 2021/0077019 | A1* | 3/2021 | Kendall | A61B 5/257 |
| 2022/0387127 | A1* | 12/2022 | Kao | G02B 21/025 |

OTHER PUBLICATIONS

Koletar et al., "Refinement of a chronic cranial window implant in the rat for longitudinal in vivo two-photon fluorescence microscopy of neuro vascular function", Apr. 2, 2019 (Year: 2019).*

Hlushchenko I, et al. Dendritic spine actin dynamics in neuronal maturation and synaptic plasticity. Cytoskeleton (Hoboken ) 73:435-441, 2016.

Holtmaat, A. et al. Long-term, high-resolution imaging in the mouse neocortex through a chronic cranial window. (2009). doi:10.1038/nprot.2009.89.

Hoskison MM, et al: Persistent working memory dysfunction following traumatic brain injury: evidence for a time-dependent mechanism. Neuroscience 159:483-491, 2009.

Hwang EJ et al, "The utility of multichannel local field potentials for brain-machine interfaces," Journal of Neural Engineering, vol. 10, No. 4, p. 046005, Aug. 2013.

Hylin MJ, et al: Behavioral and histopathological alterations resulting from mild fluid percussion injury. J Neurotrauma 30:702-715, 2013.

Juczewski, K., et al. Stress and behavioral correlates in the head-fixed method. bioRxiv 2020.02.24.963371 (2020) doi:10.1101/2020.02.24.963371.

Juneau, J., et al. Enhanced Image Sensor Module for Head-Mounted Microscopes*. in Proceedings of the Annual International Conference of the IEEE Engineering in Medicine and Biology Society, EMBS (2018). doi:10.1109/EMBC.2018.8512387.

Kellis, S et al, "Decoding spoken words using local field potentials recorded from the cortical surface," Journal of Neural Engineering, vol. 7, No. 5, p. 056007, Oct. 2010.

Khan Y et al., "Inkjet-Printed Flexible Gold Electrode Arrays for Bioelectronic Interfaces," Advanced Functional Materials, vol. 26, No. 7, pp. 1004-1013, Feb. 2016.

Kim, T. H. et al. Long-Term Optical Access to an Estimated One Million Neurons in the Live Mouse Cortex. Cell Rep. 17, 3385-3394 (2016).

Kimtan, T et al, "Printable and transparent micro-electrocorticography (μECoG) for optogenetic applications," in 2014 36th Annual International Conference of the IEEE Engineering in Medicine and Biology Society, Chicago, IL, 2014, pp. 182-485.

Lerner, T. N. et al. Intact-Brain Analyses Reveal Distinct Information Carried by SNc Dopamine Subcircuits. Cell (2015) doi:10.1016/j.cell.2015.07.014.

Li, P. et al. Measuring sharp waves and oscillatory population activity with the genetically encoded calcium indicator GCaMP6f. Front. Cell. Neurosci. (2019) doi:10.3389/fncel.2019.00274.

Lim, D., et al. Optically sectioned in vivo imaging with speckle illumination HiLo microscopy. J. Biomed. Opt. 16, 16014 (2011).

Loane DJ, et al: Progressive neurodegeneration after experimental brain trauma: association with chronic microglial activation. J Neuropathol Exp Neurol 73:14-29, 2014.

Ma, Y. Analysis of Resting-State Neurovascular Coupling and Locomotion-Associated Neural Dynamics Using Wide-Field Optical Mapping. ProQuest Dissertations and Theses (2018).

Ma, Y. et al. Resting-state hemodynamics are spatiotemporally coupled to synchronized and symmetric neural activity in excitatory neurons. Proc. Natl. Acad. Sci. U. S. A. (2016) doi:10.1073/pnas.1525369113.

Maas AI, et al: Moderate and severe traumatic brain injury in adults. Lancet Neurol 7:728-741, 2008.

(56) References Cited

OTHER PUBLICATIONS

Madisen, L. et al. Transgenic mice for intersectional targeting of neural sensors and effectors with high specificity and performance. Neuron 85, 942-958 (2015).
Makino H, et al: Transformation of Cortex-wide Emergent Properties during Motor Learning. Neuron 94:880-890, 2017.
Marvin, J. S. et al. An optimized fluorescent probe for visualizing glutamate neurotransmission. Nat. Methods (2013) doi:10.1038/nmeth.2333.
Mathis, A. et al. DeepLabCut: markerless pose estimation of user-defined body parts with deep learning. Nat. Neurosci. (2018) doi:10.1038/s41593-018-0209-y.
Meyer, A. F., et al. Two distinct types of eye-head coupling in freely moving mice. bioRxiv (2020) doi:10.1101/2020.02.20.957712.
Mohajerani, M. H. et al. Spontaneous cortical activity alternates between motifs defined by regional axonal projections. Nat. Neurosci. (2013) doi:10.1038/nn.3499.
Mohajerani, M. H., et al. Mirrored bilateral slow-wave cortical activity within local circuits revealed by fast pihemispheric voltage-sensitive dye imaging in anesthetized and awake mice. J. Neurosci. (2010) doi:10.1523/JNEUROSCI.6437-09.2010.
Murphy, T. H. et al. High-throughput automated home-cage mesoscopic functional imaging of mouse cortex. Nat. Commun. (2016) doi:10.1038/ncomms11611.
Musall, S., et al. Single-trial neural dynamics are dominated by richly varied movements. Nat. Neurosci. (2019) doi:10.1038/s41593-019-0502-4.
Namiki, S. et al. Optical glutamate sensor for spatiotemporal analysis of synaptic transmission. Eur. J. Neurosci. (2007) doi:10.1111/j.1460-9568.2007.05511.x.
Orsolic, I., et al. Mesoscale cortical dynamics reflect the interaction of sensory evidence and temporal expectation during perceptual decision-making. bioRxiv (2019) doi:10.1101/552026.
Palacios EM, et al: Resting-State Functional Connectivity Alterations Associated with Six-Month Outcomes in Mild Traumatic Brain Injury. J Neurotrauma 34:1546-1557, 2017.
Paterno R, et al: Mild Traumatic Brain Injury Decreases Broadband Power in Area CA1. J Neurotrauma 33:1645-1649, 2016.
Patti, C. L. et al. Effects of sleep deprivation on memory in mice: Role of state-dependent learning. Sleep (2010) doi:10.1093/sleep/33.12.1669.
Piatkevich, K. D. et al. A robotic multidimensional directed evolution approach applied to fluorescent voltage reporters. Nat. Chem. Biol. 1 (2018). doi:10.1038/s41589-018-0004-9.
Pinheiro-Da-Silva, J., et al. "Sleep deprivation effects on object discrimination task in zebrafish (*Danio rerio*)." Animal cognition 20.2 (2017): 159-169.
Pinto, L. et al. Task-Dependent Changes in the Large-Scale Dynamics and Necessity of Cortical Regions. Neuron (2019) doi:10.1016/j.neuron.2019.08.025.
Prevedel, R. et al. Fast volumetric calcium imaging across multiple cortical layers using sculpted light. Nat. Methods (2016). doi:10.1038/nmeth.4040.
Ramos, A. Animal models of anxiety: do I need multiple tests? Trends Pharmacol. Sci. (2008) doi:10.1016/j.tips.2008.07.005.
Resendez, S. L. et al. Visualization of cortical, subcortical and deep brain neural circuit dynamics during naturalistic mammalian behavior with head-mounted microscopes and chronically implanted lenses. Nat. Protoc. 11, 566-597 (2016).
Roberts, T et al, "Flexible Inkjet-Printed Multielectrode Arrays for Neuromuscular Cartography," Advanced Healthcare Materials, vol. 5, No. 12, pp. 1462-1470, Jun. 2016.
Rynes, M. L. et al. Assembly and operation of an open-source, computer numerical controlled (CNC) robot for performing cranial microsurgical procedures. Nat. Protoc. (2020) doi:10.1038/s41596-020-0318-4.
Schindelin, J. et al. Fiji: An open-source platform for biological-image analysis. Nature Methods (2012) doi:10.1038/nmeth.2019.

Scott, B. B. et al. Imaging Cortical Dynamics in GCaMP Transgenic Rats with a Head-Mounted Widefield Macroscope. Neuron (2018) doi:10.1016/j.neuron.2018.09.050.
Shemesh, O. A. et al. Temporally precise single-cell-resolution optogenetics. Nat. Neurosci. 20, 1796-1806 (2017).
Shimaoka, D., et al. Effects of Arousal on Mouse Sensory Cortex Depend on Modality. CellReports 22, 3160-3167 (2018).
Shimaoka, D., et al. The impact of bilateral ongoing activity on evoked responses in mouse cortex. Elife (2019) doi:10.7554/eLife.43533.
Silasi, G., et al. Intact skull chronic windows for mesoscopic wide-field imaging in awake mice. J. Neurosci. Methods 267, 141-149 (2016).
Singh, S., et al. Low-cost solution for rodent home-cage behaviour monitoring. PLoS One (2019) doi:10.1371/journal.pone.0220751.
Skocek, O. et al. High-speed volumetric imaging of neuronal activity in freely moving rodents. Nat. Methods 1 (2018), doi:10.1038/s41592-018-0008-0.
Sofroniew, N. J. et al. A large field of view two-photon mesoscope with subcellular resolution for in vivo imaging. Elife 5, 264-266 (2016).
Stirman, J. N., et al. Wide field-of-view, multi-region, two-photon imaging of neuronal activity in the mammalian brain. Nat. Biotechnol. (2016). doi:10.1038/nbt.3594.
Abadchi, J. K. et al. Spatiotemporal patterns of neocortical activity around hippocampal sharp-wave ripples. Elife (2020) doi:10.7554/eLife.51972.
Adam, Y. et al. Voltage imaging and optogenetics reveal behaviour-dependent changes in hippocampal dynamics. Nature (2019) doi:10.1038/s41586-019-1166-7.
Adams, J. K. et al. Single-frame 3D fluorescence microscopy with ultraminiature lensless FlatScope. Sci. Adv. 3, (2017).
Aghajan, Z. M. et al. Impaired spatial selectivity and intact phase precession in two-dimensional virtual reality. Nat. Neurosci. (2015) doi:10.1038/nn.3884.
Akerboom, J. et al. Genetically encoded calcium indicators for multi-color neural activity imaging and combination with optogenetics. Front. Mol. Neurosci. 6, 2 (2013).
Alali AS, et al: Economic Evaluations in the Diagnosis and Management of Traumatic Brain Injury: A Systematic Review and Analysis of Quality. Value Health 18:721-734, 2015.
Allen, W. E. et al. Global Representations of Goal-Directed Behavior in Distinct Cell Types of Mouse Neocortex. Neuron (2017) doi:10.1016/j.neuron.2017.04.017.
Bachmann B. et al., "All-inkjet-printed gold microelectrode arrays for extracellular recording of action potentials," Flexible and Printed Electronics, vol. 2, No. 3, p. 035003, Sep. 2017.
Barbera, G., et al. A wireless miniScope for deep brain imaging in freely moving mice. J. Neurosci. Methods (2019) doi:10.1016/j.jneumeth.2019.05.008.
Blakely, T et al, "Localization and classification of phonemes using high spatial resolution electrocorticography (ECOG) grids," in 2008 30th Annual International Conference of the IEEE Engineering in Medicine and Biology Society, Vancouver, BC, 2008, pp. 4964-4967.
Blennow K, et al. The neuropathology and neurobiology of traumatic brain injury. Neuron 76:886-899, 2012.
Blennow K, et al. Traumatic brain injuries. Nat Rev Dis Primers 2:16084, 2016.
Bolanos, F. et al. Mesoscale cortical calcium imaging reveals widespread synchronized infraslow activity during social touch in mice. bioRxiv (2018) doi:10.1101/430306.
Borden, P. Y. et al. Genetically expressed voltage sensor ArcLight for imaging large scale cortical activity in the anesthetized and awake mouse. Neurophotonics (2017) doi:10.1117/1.nph.4.3.031212.
Cai, D. J. et al. A shared neural ensemble links distinct contextual memories encoded close in time. Nature 534, 115-118 (2016).
Calhoun VD, et al. Ten Key Observations on the Analysis of Resting-state Functional MR Imaging Data Using Independent Component Analysis. Neuroimaging Clin N Am 27:561-579, 2017.

(56) References Cited

OTHER PUBLICATIONS

Centers for Disease Control and Prevention. Nonfatal injury data. Webpage. Version dated Nov. 21, 2015. Available online at: https://web.archive.org/web/20151121083505/https://www.cdc.gov/injury/wisqars/nonfatal.html.
Chen T-W et al., "Ultrasensitive fluorescent proteins for imaging neuronal activity," Nature, vol. 499, No. 7458, pp. 295-300, Jul. 2013.
Chen Y, et al: A modified controlled cortical impact technique to model mild traumatic brain injury mechanics in mice. Front Neurol 5:100, 2014.
Colavito, V. et al. Experimental sleep deprivation as a tool to test memory deficits in rodents. Front. Syst. Neurosci. (2013) doi:10.3389/fnsys.2013.00106.
Coskun, A. F., et al. Wide field-of-view lens-free fluorescent imaging on a chip. Lab Chip 10, 824 (2010).
Creed JA, et al: Concussive brain trauma in the mouse results in acute cognitive deficits and sustained impairment of axonal function. J Neurotrauma 28:547-563, 2011.
Daigle, T. L. et al. A Suite of Transgenic Driver and Reporter Mouse Lines with Enhanced Brain-Cell-Type Targeting and Functionality. Cell (2018) doi:10.1016/j.cell.2018.06.035.
Dana, H. et al. High-performance calcium sensors for imaging activity in neuronal populations and microcompartments. Nat. Methods (2019) doi:10.1038/s41592-019-0435-6.
Dana, H. et al. Sensitive red protein calcium indicators for imaging neural activity. Elife (2016) doi:10.7554/elife.12727.
Dana, H. et al. Thy1-GCaMP6 transgenic mice for neuronal population imaging in vivo. PLoS One 9, (2014).
Dash, M. B., et al. Long-term homeostasis of extracellular glutamate in the rat cerebral cortex across sleep and waking states. J. Neurosci. (2009) doi:10.1523/JNEUROSCI.5486-08.2009.
Dawson, T. M., et al. Animal models of neurodegenerative diseases. Nature Neuroscience (2018) doi:10.1038/s41593-018-0236-8.
De Groot, A. et al. Ninscope, a versatile miniscope for multi-region circuit investigations. Elife (2020) doi:10.7554/eLife.49987.
Dipoppa, M. et al. Vision and Locomotion Shape the Interactions between Neuron Types in Mouse Visual Cortex. Neuron 98, 602-615.e8 (2018).
Donaldson, P. D., et al. Inkjet-Printed Silver Electrode Array for in-vivo Electrocorticography. in 2019 9th International IEEE/EMBS Conference on Neural Engineering (NER) 774-777 (2019). doi:10.1109/NER.2019.8717083.
Dubbs, A., et al. moco: Fast motion correction for calcium imaging. Front. Neuroinform. (2016) doi:10.3389/fninf.2016.00006.
Escabi MA et al., "A high-density, high-channel count, multiplexed uECoG array for auditory-cortex recordings," Journal of Neurophysiology, vol. 112, No. 6, pp. 1566-1583, Sep. 2014.
Ferezou, I. et al. Spatiotemporal dynamics of cortical sensorimotor integration in behaving mice. Neuron 56, 907-23 (2007).
Fink, A. J., et al. A virtual burrow assay for head-fixed mice measures habituation, discrimination, exploration and avoidance without training. Elife (2019) doi:10.7554/eLife.45658.
Fletcher, C. F. et al. Absence epilepsy in tottering mutant mice is associated with calcium channel defects. Cell 87, 607-617 (1996).
Fu, T.-M. et al. Stable long-term chronic brain mapping at the single-neuron level. Nat. Methods 13, 875-882 (2016).
Galgano M, et al: Traumatic Brain Injury: Current Treatment Strategies and Future Endeavors. Cell Transplant 26:1118-1130, 2017.
Ganji M et al., "Development and Translation of PEDOT:PSS Microelectrodes for Intraoperative Monitoring," Advanced Functional Materials, vol. 28, No. 12, p. 1700232, Mar. 2018.
Gao X, et al. Moderate traumatic brain injury causes acute dendritic and synaptic degeneration in the hippocampal dentate gyrus. PLoS One 6:e24566, 2011.
Gardner AJ, et al. Neuroepidemiology of traumatic brain injury. Handb Clin Neurol 138:207-223, 2016.

Ghanbari, L., et al. "Cortex-wide neural interfacing via transparent polymer skulls." Nature communications 10.1 (2019): 1-13.
Ghanbari, L., et al. "Craniobot: A computer numerical controlled robot for cranial microsurgeries." Scientific reports 9.1 (2019): 1-12.
Ghosh, K. K. et al. Miniaturized integration of a fluorescence microscope. Nat. Methods (2011) doi:10.1038/meth.1694.
Gilad, A. et al. Spatiotemporal refinement of signal flow through association cortex during learning. Nat. Commun. (2020) doi:10.1038/s41467-020-15534-z.
Gong, Y. et al. High-speed recording of neural spikes in awake mice and flies with a fluorescent voltage sensor. Science (80-. ). 350, 1361-1366 (2015).
Green, M. C. et al. Tottering-a neuromuscular mutation in the mouse: And its linkage with oligosyndactylism. J. Hered. 53, 233-237 (1962).
Guo, Z. V. et al. Procedures for behavioral experiments in head-fixed mice. PLoS One (2014) doi:10.1371/journal.pone.0088678.
Heo DN et al., "Flexible and Highly Biocompatible Nanofiber-Based Electrodes for Neural Surface Interfacing," ACS Nano, vol. 11, No. 3, pp. 2961-2971, Mar. 2017.
Hermiz J. et al., "Sub-millimeter ECoG pitch in human enables higher fidelity cognitive neural state estimation," NeuroImage, vol. 176, pp. 454-464, Aug. 2018.
Subramanian, V. et al. High-Speed Printing of Transistors: From Inks to Devices. Proc. IEEE 103, 567-582 (2015).
Tran HT, et al: Distinct temporal and anatomical distributions of amyloid-beta and tau abnormalities following controlled cortical impact in transgenic mice. PLoS One 6:e25475, 2011.
Tsien RY, "The Green Fluorescent Protein," Annual Review of Biochemistry, vol. 67, No. 1, pp. 509-544, Jun. 1998.
Valley, M. T. et al. Separation of hemodynamic signals from GCaMP fluorescence measured with wide-field imaging. J. Neurophysiol. (2020) doi:10.1152/jn.00304.2019.
Vanni, M. P. et al. Mesoscale Transcranial Spontaneous Activity Mapping in GCaMP3 Transgenic Mice Reveals Extensive Reciprocal Connections between Areas of Somatomotor Cortex. J. Neurosci. (2014) doi:10.1523/JNEUROSCI.1818-14.2014.
Vanni, M. P., et al. Mesoscale mapping of mouse cortex reveals frequency-dependent cycling between distinct macroscale functional modules. J. Neurosci. (2017) doi:10.1523/JNEUROSCI.3560-16.2017.
Vascak M, et al: Mild Traumatic Brain Injury Induces Structural and Functional Disconnection of Local Neocortical Inhibitory Networks via Parvalbumin Interneuron Diffuse Axonal Injury. Cereb Cortex1-20, 2017.
Vora, S. R., et al. Postnatal Ontogeny of the Cranial Base and Craniofacial Skeleton in Male C57BL/6J Mice: A Reference Standard for Quantitative Analysis. Front. Physiol. 6, 417 (2016).
Waxweiler RJ, et al: Monitoring the impact of traumatic brain injury: a review and update. J Neurotrauma 12:509-516, 1995.
Wekselblatt, J. B., et al. Large-scale imaging of cortical dynamics during sensory perception and behavior. J. Neurophysiol. (2016) doi:10.1152/jn.01056.2015.
Whiteneck GG, et al: Risk of Negative Outcomes After Traumatic Brain Injury: A Statewide Population-Based Survey. J Head Trauma Rehabil 31:E43-E54, 2016.
Xie, Y. et al. Resolution of high-frequency mesoscale intracortical maps using the genetically encoded glutamate sensor iGluSnFR. J. Neurosci. (2016) doi:10.1523/JNEUROSCI.2744-15.2016.
Xiong Y, et al. Animal models of traumatic brain injury. Nat Rev Neurosci 14:128-142, 2013.
Yuk, H., et al. "3D printing of conducting polymers." Nature communications 11.1 (2020): 1-8.
Zong, W. et al. Fast high-resolution miniature two-photon microscopy for brain imaging in freely behaving mice. Nat. Methods 14, 713 (2017).

* cited by examiner

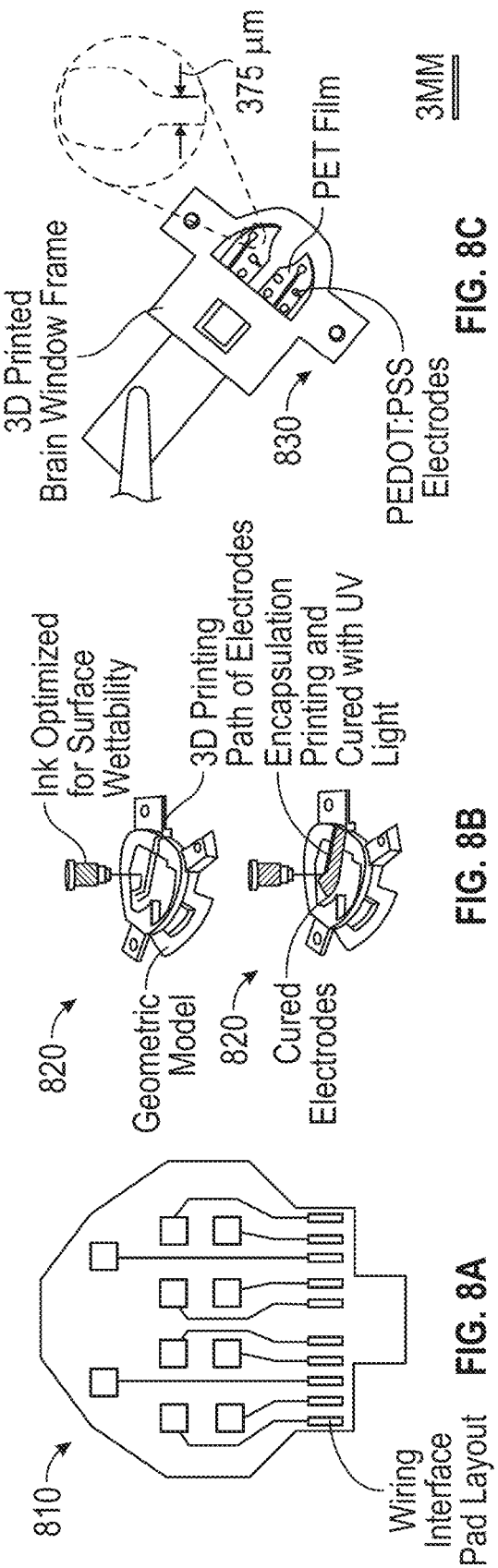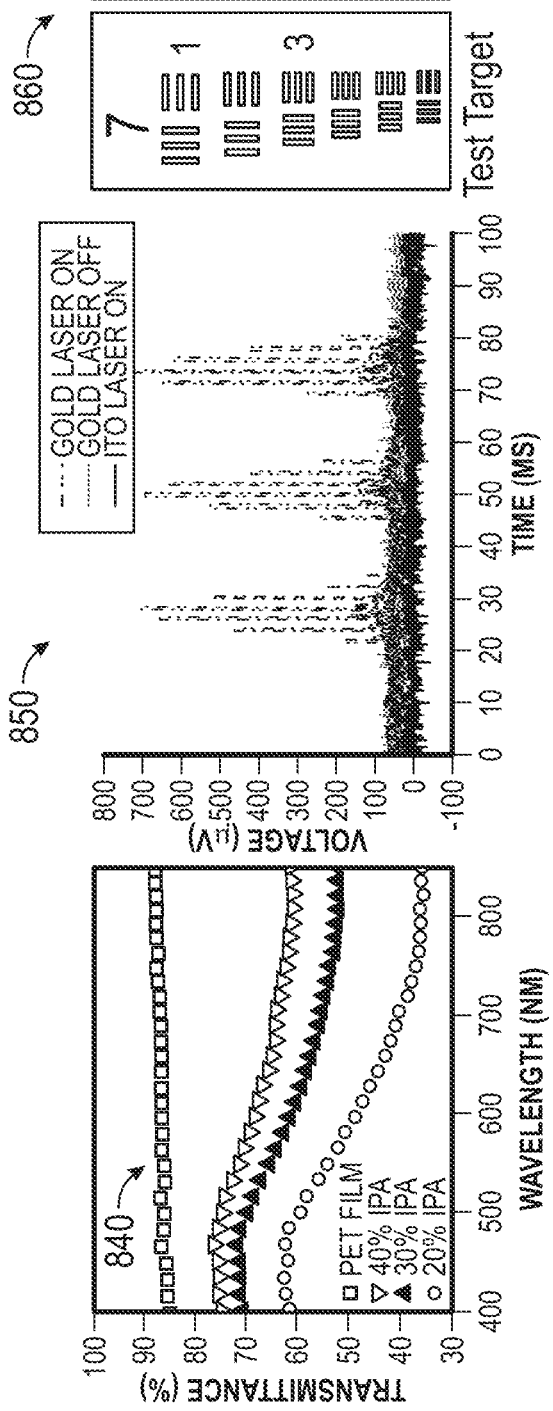
FIG. 8A
FIG. 8B
FIG. 8C
FIG. 8D
FIG. 8E
FIG. 8F

SYSTEMS AND METHODS FOR MULTIMODAL NEURAL SENSING

CROSS-REFERENCE TO RELATED APPLICATIONS

This application claims the benefit of U.S. Provisional Patent Application Ser. No. 62/944,137 filed on Dec. 5, 2019 and entitled "Systems and Methods for Multimodal Neural Sensing," which is incorporated herein by reference as if set forth in its entirety for all purposes.

STATEMENT REGARDING FEDERALLY SPONSORED RESEARCH

This invention was made with government support under R21NS103098, R01NS111028, and R42NS110165 awarded by National Institutes of Health (NIH). The government has certain rights in the invention.

BACKGROUND

The mammalian cerebral cortex is critical for mediating learned and adaptive forms of sensory motor behaviors, and the evolutionary expansion of the cortex underlies many advanced cognitive capabilities in humans and primates. Neuroscientists have taken advantage of the modular organization and segregation of the cortex into anatomically and functionally distinct regions and have made enormous progress understanding in how computations performed in specific cortical regions produce behavior. However, the operation of the brain cannot be understood only by analysis of its components in isolation. Behavior involves the processing and integration of information across brain regions and the mechanisms by which neuronal activity is coordinated across the cerebral cortex to produce a unitary behavioral output are not well understood.

The activity patterns of hundreds of thousands of neurons organized in circuits distributed across multiple brain regions mediate our interaction with the outside world. A mechanistic understanding of the neuronal underpinnings of sensory perception, action, and cognition requires both measuring and manipulating the activities of these neuronal circuits at single cell resolution across several millimeters. Further, the activities of these neurons are dynamically changing at time scales ranging from milliseconds to days, as they are subject to neuromodulatory agents, motor and sensory activity, plasticity, and disease. A critical challenge for modern neuroscience is to be able to monitor the brain across these multiple temporal and spatial levels. Currently, there is a gap between tools that provide interrogations at the single cell and microcircuit levels, and those designed to interface with large and multiple brain regions. No technology exists that provides single cell resolution activity monitoring capabilities over large brain regions.

Understanding the spatio-temporal organizing principles of the motor cortices is also requisite to understand voluntary motor control. Preparatory activity is not reflected in electromyographic (EMG) muscle recordings. Yet, direct projections from both dorsal motor cortex (PMd) and primary motor cortex (MI) to spinal motor neurons and the fact that microstimulation of MI results in muscle activation suggest that motor cortical activity should be reflected in increased EMG activity. Understanding of the transition from preparation to movement is complicated by the heterogeneity of motor cortical neuronal activity both before and after movements.

Therefore, understanding behavior requires tools to study large regions of the central nervous system at high spatial and temporal resolution. Even simple sensory or motor tasks involve processing of information in multiple cortical areas. For example, deflection of a single whisker for a mouse results in activation distributed across the sensorimotor cortices. Locomotion modulates the neuronal responses in the primary visual cortex with cell-type specificity, and arousal exerts markedly different effects across the cerebral cortex, both spatially and temporally. Further, such long range information flow is dependent on the internal brain state as well as information learned from past experiences.

There is also a pressing need for understanding and monitoring traumatic brain injury (TBI), which is the leading cause of morbidity and mortality in young individuals in developed countries. TBI is a frequent sequela of accidental injury in the US and may be stratified into mild, moderate, and severe injury levels. Mild TBI (mTBI), commonly referred to as concussion, represents 80-90% of all TBI cases. A large US study found that over 40% of the population had at least one TBI during their lifetime. Typically, mTBI is caused by blunt head trauma resulting in altered brain function. mTBI is clinically diagnosed in patients with a Glasgow Coma Score of 13-15 without associated structural pathology. In addition to the immediate physical, cognitive and behavioral symptoms, a large number of patients with concussive injury develop a persistent CNS dysfunction, post-concussive syndrome (PCS). Also, the effects of repeated mTBI are cumulative and can lead to chronic traumatic encephalopathy (CTE), a neurodegenerative condition. Given the prevalence, potential long-term adverse effects, and economic costs, it is imperative to understand the acute and secondary pathophysiological mechanisms underlying mTBI if we are to improve therapeutic options to minimize the long-term sequelae of mild brain injury.

Several anatomical and physiological findings establish the relevance of animal models for studying the progression of injury associated with TBI in humans. However, previous studies are almost exclusively based on histological, immunochemical, and electron microscopy analyses at single time points after injury. Diffuse axonal injury (DIA), commonly observed in TBI patients, is a major finding in animal models related to behavioral outcome. Additionally, microglial and astrocyte activation, amyloid-$\beta$ accumulation and tau aggregation, as well as dendritic spine loss occur with TBI. There is limited information on the physiological alterations and deficits at the cellular level, with the exception of a few electrophysiological studies. Also lacking are studies integrating changes in neuronal population dynamics with changes at the cellular and synaptic levels.

There are no effective interventions to reverse or restore function of brain tissue damaged or lost during the initial traumatic insult with much of the therapeutic focus centered on minimizing secondary insults. Therefore, there is a pressing need to understand at multiple scales the structural and functional changes as they evolve from the acute to chronic state within the same circuits and cells following mTBI. However, conventional detection and monitoring systems are not able to meet this need.

Improving the fundamental understanding of the brain, such as with mTBI responses, through detection and monitoring may allow for examination of the pathophysiology of mTBI and other effects from the synaptic level up to behavioral effects. Thus, there remains a need for detection and monitoring mechanisms for the brain in general that may open the possibility to identify new therapeutic approaches and diagnostic methods.

SUMMARY OF THE DISCLOSURE

The present disclosure addresses the aforementioned drawbacks by providing a system and method for imaging and monitoring a tissue, such as a cerebral cortex, of a subject. Access to imaging a tissue, such as cerebral cortex, may be provided by removing a portion of a bone, such as a portion of a skull of the subject. An optically transparent prosthesis may be used to replace the portion of the skull removed and may be conformed to the same 3D contour of the bone that was removed. An imaging system may then be affixed to the skull prosthesis and may be used to acquire image data of the tissue of the subject at high spatial and temporal resolution and without interference from intervening bone material. The image data may include images of single neurons, a large region of the brain, or assessed to determine brain function, behavior, spatio-temporal organizing principles of the cortex, therapeutic approaches, and the like.

In one configuration, a system is provided for acquiring data from a tissue of a subject. The system includes a computer system configured to access images of bone or connective tissue adjacent to a surface of the tissue of the subject, and generate a contour of the at least one of bone or connective tissue. The system also includes a prosthesis configured to conform to and replace the contour of the bone or connective tissue, and a data acquisition system in communication with the computer system and mounted to the prosthesis for acquiring data of the tissue of the subject.

In some configurations, an imaging system is included and mounted to an optically transparent prosthesis for acquiring image data of the tissue of the subject. In some configurations, at least one electrode is coupled to the optically transparent prosthesis and configured to acquire electrical data of the tissue of the subject. The optically transparent prosthesis may include a plurality of electrodes in an array, and the array may be an electrocorticography (ECoG) array.

In one configuration, a method is provided for acquiring data from a tissue of a subject. The method includes accessing images of bone or connective tissue adjacent to a surface of the tissue of the subject and generating a contour of the at least one of bone or connective tissue. The method also includes replacing the contour of the bone or connective tissue with a prosthesis configured to conform to the contour of the bone or connective tissue. The method also includes acquiring data of the tissue of the subject with a data acquisition system in communication with the computer system and mounted to the prosthesis.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 8A is a non-limiting example CAD rendering of a 10 channel ECoG array that illustrates a PAD layout that may be used for interfacing with external amplifiers.

FIG. 8B is a non-limiting example schematic of printed transparent electrodes onto a reconstructed model of a brain window.

FIG. 8C is a view of non-limiting example transparent electrodes printed with PEDOT:PSS onto a PET film that conformally covers the window.

FIG. 8D is a graph of non-limiting example data of transmittance of PET film and PEDOT:PSS film deposited with ink tuned by different concentrations of IPA.

FIG. 8E is a graph of non-limiting example data for light transmittivity.

FIG. 8F is a chart of a non-limiting example resolution test for the printed PEDOT:PSS film.

DETAILED DESCRIPTION

Figure 1:
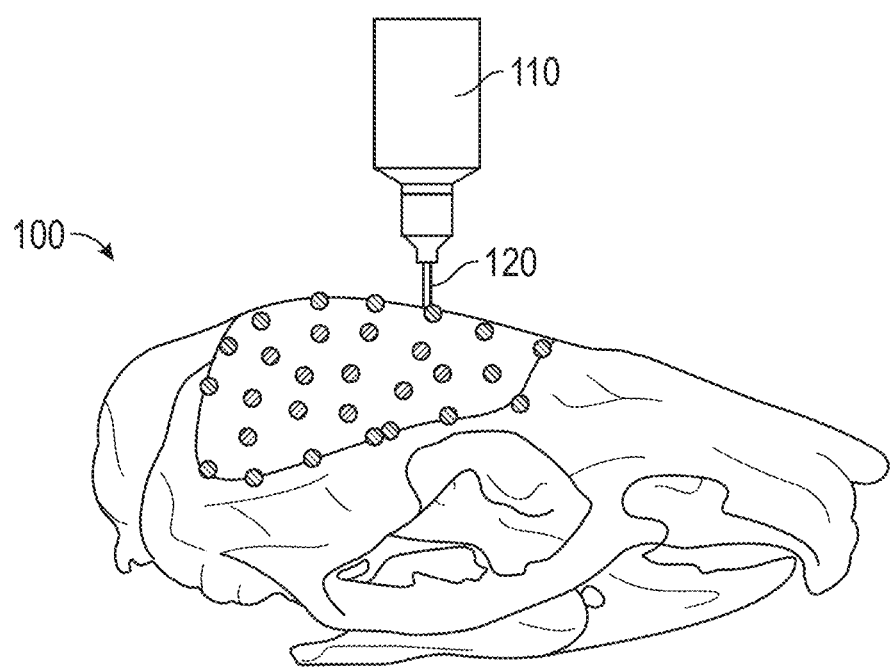
FIG. 1 is an image of a non-limiting example skull surface point assessment for determining a configuration of a transparent skull prosthesis.

A system and method is provided for imaging and monitoring a tissue, such as a cerebral cortex, of a subject. Access to imaging a tissue, such as the cerebral cortex, may be provided by removing a portion of a bone, such as a portion of a skull of the subject. An optically transparent prosthesis may then be used to replace the portion of the skull removed and may be conformed to the same 3D contour of the bone that was removed. An imaging system may then be affixed to the skull prosthesis and may be used to acquire image data of the tissue of the subject at high spatial and temporal resolution and without interference from intervening bone material. The imaging system can simultaneously perform both fluorescence imaging and reflectance imaging to correct for hemodynamic changes. By affixing the imaging system to the skull, the system may be able to gather data in animals performing complex behaviors that would be impossible in head-fixed animals.

Traditionally, monitoring neural activity relied on recording electrodes. Extracellular spiking activity of isolated neurons along with local field potentials (LFPs) generated by spatially confined populations of neurons, provide a wealth of information on the state of a subject and its behavior. The signal fidelity and temporal resolution offered by recording electrodes make them the gold standard for neural sensing. Both 1- and 2-dimensional arrays using metal or silicon substrates have been developed for extracellular recordings from multiple brain regions during free behavior. While these arrays can provide spatial resolution in a small region(s), these electrode arrays cannot easily be scaled to recordings across large regions owing to their invasive nature. Minimally invasive neural surface electrode arrays, such as electrocorticography (ECoG) devices, allow LFP quality recordings from multiple sites distributed across the cortical surface.

Until recently, the study of meso- and macroscopic brain networks has been limited to functional magnetic resonance imaging (fMRI) and magnetoencephalography (MEG). However, fMRI and MEG are limited by their spatial and temporal resolution and can only be done under head-fixed conditions, which precludes understanding cortical computations underlying complex cognitive behaviors. The development of optical sensing tools in recent years allow cellular resolution monitoring and manipulations in local circuits. Genetically encoded Ca2+ indicators (such as GCaMP6) have enabled in vivo high resolution monitoring of activities of hundreds to thousands of neurons. The development of red-shifted variants of Ca2+ indicators and optogenetic tools open deep cortical regions for optical sensing and perturbation. The advent of streamlined strategies to rapidly generate transgenic mice expressing optical reporters has allowed the development of complementary imaging instrumentation to perform wide-field optical imaging. Therefore, while optical probes provide impressive spatial precision and span in sampling genetically defined populations of neurons, currently available probes are limited in their temporal precision. One of the most critical limitations of current wide-field optical imaging is the restriction to head-fixed mice. The lack of vestibular inputs and disruptions in eye-head movement coupling, and behavioral effects from increased stress can significantly alter neural activity during head-fixation as compared to freely behaving animals. These head-fixed devices are also only designed to perform cellular resolution imaging, and thus have small field of view (FOV, <1 mm$^2$), limiting their application to imaging small brain regions.

In one configuration, a system is provided that combines the spatial sampling and genetic specificity of wide-field optical sensing with the high temporal resolution of electrical sensing in a miniaturized device to sample neuronal activities throughout the cortex during free and naturalistic behavior of a subject. The system includes a method of imaging Ca2+ dynamics from large sections of the optically-accessible regions of the brain surface. The system also includes integrated electrode arrays for electrically monitoring neuronal activity from the cortical surface without interfering with optical access, and miniaturized instrumentation that can perform simultaneous electro-optical activity mapping in headfixed or freely moving subjects.

In some configurations, an automated surgery platform may be used for precisely excising and replacing a portion of a skull of a subject. In a non-limiting example for small animal imaging, the dorsal cortex may be covered with transparent polymer skulls. The transparent polymer skull allows long-term, chronic optical access to the entire dorsal cerebral cortex for high resolution optical imaging. Miniaturized head-mounted devices may be used for simultaneous cortex wide optical imaging and ECoG recordings.

The brain cannot be understood only by analysis of its components in isolation. Behavior requires interactions across brain regions. Optical imaging reveals complex, widespread activity patterns in the cerebral cortex during rest and during different behavioral states in head-fixed subjects. However, wide-field optical imaging is limited by both temporal resolution and head-fixed behaviors. In some configurations, by combining a head-mounted microscope and ECoG recording arrays, the limitations above may be overcome, allowing simultaneous, wide-field optical and ECoG measurements in the freely moving subject. A variety of behavioral tasks such as novel object recognition, spatial exploration, t-maze etc may be used to measure neuronal activities that are distributed across the cerebral cortical network. These representations are not only incorporated into the cortical activity during the actual behavior, but are also involved in predicting and recalling the behavior.

Referring to FIG. 1, a skull surface point assessment 100 is shown. In some configurations, a robotic neurosurgery platform for automated, precise, skull excision may be used. A robotic platform may include a computer and numerically controlled (CNC) neurosurgery robot capable of precisely excising sub-millimeter thick, digitally defined sections of a skull without causing any damage to the underlying dura and brain tissue. In a non-limiting example for small animal applications, a rodent stereotaxic frame may be used with a 3-axes manipulator 110 to drive a contact sensor/micro-end mill 120. The robot utilizes a contact sensor to probe and generate a point cloud on the surface of a skull, as depicted in FIG. 1. A spline interpolation algorithm may be used with a subset of points at the perimeter of the contour defined by the point cloud and generates the machining path for the end mill. The end mill then machines the skull in small increments until the bone is sufficiently thin to be removed. The depth at which the milling operation stopped may be consistently less than the actual skull thickness in attempts to perform a craniotomy covering ~80% of the dorsal cortex. Such consistently precise craniotomies are extremely difficult to perform for human practitioners.

Figure 2:
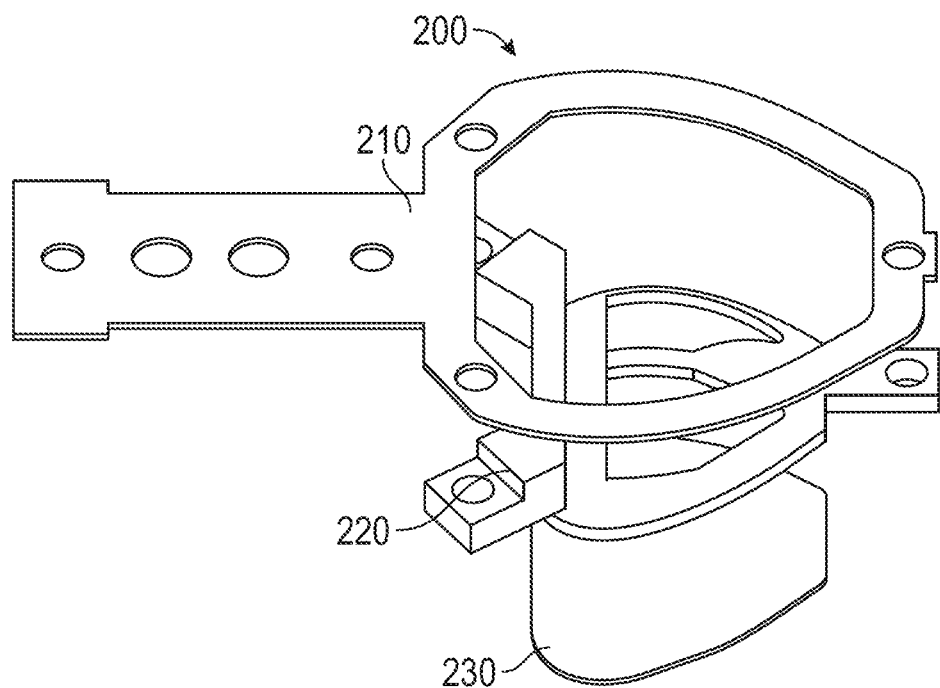
FIG. 2 is a perspective view for one configuration of a transparent skull replacement prosthesis.

Referring to FIG. 2, one configuration for a transparent skull replacement device 200 is shown. In some configurations, a 3D-printed transparent polymer skulls is used to provide for imaging of the brain surface. A headplate 210 may be composed of any suitable material, such as a biocompatible material such as titanium. A frame 220 may be coupled to the headplate 210 and form a support for the transparent polymer window 230. In non-limiting examples, the frame 220 may be a 3D printed PMMA frame and the window 230 may be formed of polyethylene terephthalate (PET). The sections of the skull excised, such as excised using the CNC robot described above, can be replaced with a corresponding morphologically conformant, 3D-printed cranial prosthesis. The 3D geometry of these implants can replace much larger sections of the skull, compared to traditional planar windows, which induce macroscopic physical deformations of the underlying brain tissue. In a non-limiting example of application to mice, given that the skull morphologies of mice of a specific strain and age are well conserved, a 3D contour generated by mapping the skull surface of one mouse can be used to generate a generalized 3D model of the skull. The model can then be used to design a prosthesis made of an optically clear material. Point clouds from the skull surface of a subject may be acquired. The point cloud may then be used to generate a surface, such as with a CAD software like SolidWorks (Dassault Systems Inc.), and the like. The surface may be used as a template to generate 'brain-window' frames that may be 3D-printed, such as out of a poly-methyl-methacrylate (PMMA) resin. In a non-limiting example, the frames may be created with a desktop 3D printer to which transparent polyethylene terephthalate (PET) films may be bonded to form an enclosed shell. The frames may be modified to either fasten titanium headposts during implantation for head-fixed imaging or modified to have mating features for head mounted optical imaging devices, and the like.

In one non-limiting example of imaging a brain surface in small animal applications, mesoscale, single-photon imaging may be performed using a low magnification optical microscope. Headplate designs may be optimized to allow an entire dorsal cortex to be imaged using high magnification two-photon (2P) microscopes with short microscope objective lens working distances, such as a working distance of just 3 mm. A single image may capture a single neuron or a plurality of neurons.

In some configurations, the transparent skull prostheses include electrodes, or sensing electronics. Flexible, inkjet-printed, or 3D printed electrodes and electronic devices may be used and may include thin electronic sensors and circuits for bio-sensing. Manufacturing of the flexible electronic sensors may include the use of liquid electronic "inks" and solution-based fabrication techniques that produce high-performance air-stable electrodes or electronic devices, including but not limited to diodes, transistors, sensors, energy harvesters, and controllers. 3D printed electrodes and electronic devices may be created to follow a contour of the transparent prosthesis.

Referring to FIGS. 8A-8F, non-limiting example configurations for 3D printed electrodes and electronic devices, and data are shown. Referring to FIG. 8A, a non-limiting example CAD rendering of a 10 channel ECoG array 810 is shown that illustrates a PAD layout that may be used for interfacing with external amplifiers. Referring to FIG. 8B, a non-limiting example schematic is shown of printed transparent electrodes 820 onto a reconstructed model of a brain window. Referring to FIG. 8C, a view of non-limiting example transparent electrodes 830 printed with PEDOT:PSS onto a PET film that conformally covers the window is shown. The ink may be diluted, such as with 30% isopropyl alcohol (IPA), to improve the printability. Referring to FIG. 8D, non-limiting example data 840 of transmittance of PET film (5 mil) and PEDOT:PSS film (300 nm) deposited with ink tuned by different concentration of IPA. The concentration of IPA may be optimized for uniform pattern formation, such as optimizing to a 30% concentration of IPA, as indicated in the non-limiting example data of FIG. 8D. Referring to FIG. 8E, non-limiting example data 850 is shown for light transmittivity, where transmittivity >80% through transparent electrodes produces negligible photoelectric artifacts. Referring to FIG. 8F, a non-limiting example resolution test 860 is shown for the printed PEDOT:PSS film with a Resolution Test Chart. The tested resolutions are over 228.1 lp/mm for both PET film and PEDOT:PSS film that was printed with ink of 30% IPA dilution. FIG. 8F demonstrates that 3D printing does not affect imaging resolution.

The electrodes and electronic devices may include electronic sensors, which may include flexible, high-density electrocorticography (ECoG) sensor arrays for in vivo measurements in a subject. These sensor arrays may be integrated into the transparent brain/skull windows described above to enable simultaneous whole cortex Ca2+ imaging with high temporal resolution electrophysiology. The ECoG sensors may provide for high spatial density and mechanical flexibility, and may include transparent regions for optical stimulation. The sensor arrays may be designed not to rely on microfabrication techniques that were designed for silicon wafers and integrated circuits in an effort to make the sensor arrays more easily manufactured. In the long run, there may be enormous value in developing tools and processes for fabricating non-planar, flexible devices that conform to the complex 3D geometry of the brain. The method of printing solution-based electronic materials is an additive process that does not require optical lithography, resulting in lower overall process complexity. This method has the capability to dramatically change the way sensors and circuits are made for low-volume applications where customized designs and quick-turn revisions are essential. For example, electrode placement and wiring routing can be quickly modified to optimize ECoG sensing at specified locations on the cortex for different experiments.

In some configurations, integration of widefield optical imaging and electrical recordings may be performed to achieve cortex wide activity mapping in freely moving subjects at high spatial temporal resolution. Wide-field cortical activity mapping may be achieved via Ca2+ imaging through transparent polymer skulls described above. The polymer skulls may allow access to sample activities from 800,000 to 1,000,000 neurons at the surface of the dorsal cortex of the subject.

Miniature head-mounted imaging devices may be used to study cellular resolution activity during free behavior. However, all current miniature imaging systems are designed to image small fields of view of 1-2 mm diameter. By contrast, systems and methods according to the present disclosure may be capable of imaging the whole dorsal cortex of a subject. Electronic sensor capabilities may be used with functionalized polymer skulls that allow simultaneous whole cortex Ca2+ imaging and ECoG recordings. Large surface areas may be covered rather than the small fields of view described above. Mesoscale cortical dynamics may be assessed that underlie object recognition. It is currently not possible to do such assessments in head-fixed animals, and the systems and methods of the present disclosure enable assessments of how global computations occurring in the cortex mediates sensory perception, action and cognitive processes. The systems and methods may be used for new classes of brain machine interfaces, enabling information reading and writing at previously incapable spatial scales.

Figure 3:
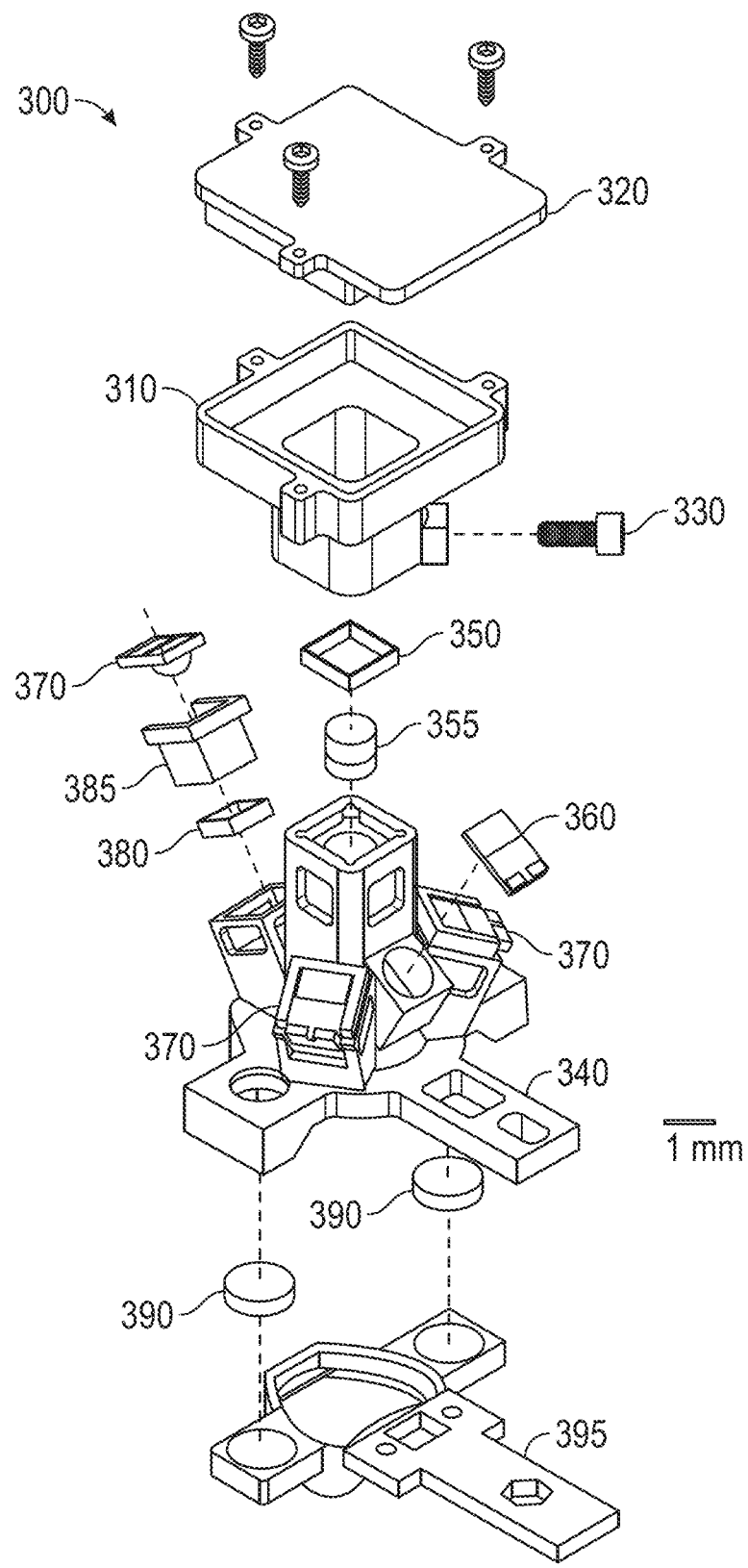
FIG. 3 is an exploded view of one configuration for an imaging device or mesoscope.

Referring to FIG. 3, one configuration for a mesoscope 300 is shown that is capable of simultaneously imaging multiple regions of an anatomy of a subject, such as multiple regions of a cortex. A housing 310, such as a Delrin™ housing may include a coupling to CMOS sensor 320. An adjustment screw 330 may provide for adjustable coupling to bottom housing 340. Bottom housing 340 may include provisions for an emission filter 350 (e.g. a bandpass filter 525 nm) and collector lens 355. Provisions may also be provided for reflectance source 360, which may be a green LED source, and excitation sources 370, which may be blue LEDs, (e.g. LEDs at 480 nm wavelength). The LEDs may be paired with excitation filters and selected to deliver a specified power amount to the tissue surface, such as a cumulative 31 mW of power to the brain, in a non-limiting example. The Excitation sources 370 may include an excitation filter 380 (e.g. a bandpass filter 470 nm) and filter holder 385 to retain the excitation filters 380. Magnets 390 may provide for removable coupling to frame 395.

In some configurations, the LEDs may be angled with respect to a central axis. In a non-limiting example, two of the blue LEDs may be oriented at 30 degrees with respect to the optical axis. The third, located at the anterior of the bottom housing, may be oriented at 25 degrees with respect to the optical axis. The LEDs may be revolved around the optical axis at angles of 90, 225, and 315 degrees. To reduce glare while maximizing power delivery to the FOV, the blue LEDs may be a select distance from the imaged surface, such as 9.55 mm from the imaged surface in a non-limiting example. The green LED may be selected to deliver a specified power, such as 0.22 mW of power, and may be located at the posterior of the bottom housing at an orientation of 55 degrees with respect to the optical axis.

The CMOS sensor may be used to capture images of the cortex alternately illuminated by the blue LEDs (e.g. filtered with a 20 nm band gap centered at 470 nm) and the green LED to capture reflectance changes simultaneously with calcium activity. A trigger circuit may be used with time stamps of CMOS frame acquisitions to precisely switch between the blue LEDs and green LED. The blue LEDs and green LED may be selected to have desired time constants (e.g to reach 66.66% peak power resulting in time constants of 1.79±0.31 ms and 1.97±_0.10 ms, respectively). The blue LEDs may be powered on only during odd-numbered frames captured by the CMOS sensor. In a non-limiting example, this may be controlled by limiting switching on of the blue LEDs and green LED to 20 ms and 4 ms, respectively, starting after the CMOS sensor initiates each frame capture. A warm up period, such as a two-minute warm-up period, may be used for the blue LEDs during each use for the power intensity to stabilize before data collection.

A mesoscope according to the present configuration is a head-mounted, miniature wide-field scope compatible with transparent polymer windows for mesoscale activity mapping in freely moving subjects. The three blue LEDs may be wired in series, and wires to power the green and three blue LEDs may be routed through a commutator to alleviate torsional strain on the device when deployed on freely moving mice. The mesoscope may be a lightweight (such as less than 4 g), miniature imaging scope or 'mesoscope' for imaging Ca2+ dynamics from the whole cortex during free behavior. In one non-limiting example, the mesoscope has a field of view of 8 mm×11 mm wide with up to 60 Hz imaging speed. In a non-limiting example, a mesoscope can image most of the mouse dorsal cortex with resolution ranging from 39 to 56 µm. One skilled in the art will recognize that other fields of view, resolutions, and imaging speeds are possible.

Stroboscopic illumination with light sources, such as blue and green LEDs in a non-limiting example, allows for the measurement of both fluorescence changes due to calcium activity, for example, and reflectance signals to capture hemodynamic changes. Mesoscale calcium activity may be recorded across the dorsal cortex during sensory-evoked stimuli, open field behaviors, and social interactions. In some configurations, combining the mesoscale imaging with electrophysiology may allow for measuring dynamics in extracellular glutamate release in the cortex during the transition from wakefulness to natural sleep.

In some configurations, correction for hemodynamics may be performed using a ratiometric method. After correction for global and illumination artifacts, the signals in the green channel may be filtered using a zero-phase Chebyshev lowpass filter with a cutoff frequency of 0.15 Hz. The illumination corrected blue signal and filtered green signals may be passed to a hemodynamic correction, such as that of Equation 1:

$$F_C = \frac{\frac{F_b}{\overline{F_b}}}{\frac{F_g}{\overline{F_g}}} \quad \text{(Eq. 1)}$$

$F_b$ is the corrected fluorescence trace for a blue frame and $\overline{F_b}$ is the mean fluorescence trace across all blue frames in the time series. The normalization of the green frames may be conducted similarly. Dividing both the normalized blue and green intensities in every pixel and frame yields $F_c$, the hemodynamic corrected pixel traces for every frame in the FOV. The hemodynamic corrected traces may be filtered using a zero-order Chebyshev bandpass filter (e.g. a filter with cutoff frequencies of 0.1 Hz and 5 Hz).

In some configurations, a vessel diameter tracking may be performed. Blue channel videos may be inverted, and the background may be subtracted, such as by using a rolling ball radius of 30 pixels. A select ROI may then be drawn around the vessel to be analyzed. In a non-limiting example, the ROI is a rectangle used as a guide to create 6 evenly spaced, horizontal lines along the height of the rectangle. The lines may be a select number of pixels (e.g. 5 pixels) thick and as long as the width of the rectangle. These lines may be used as ROIs to track the vessel diameter throughout a trial. To calculate vessel diameter, the intensity profile along a line may be plotted. Then, the maximum intensity and its corresponding location in pixels along the line may be found. Using half of the maximum intensity as a threshold, the pixel with the lowest intensity greater than the threshold in both directions from the maximum intensity may be found. The difference between the pixel locations of these two values was then stored as the vessel diameter. This process may be repeated for each line and each frame in a video.

Head-mounted cameras compatible with the polymer skulls discussed above may enable mesoscale cortical imaging in freely behaving subjects. When the polymer skull frames are 3D printed, their geometry can be modified to have a planar top face. The device may include a plurality (such as three, in a non-limiting example) of blue LED illuminators that deliver light to the cortex via custom cut excitation filters. An additional unfiltered LED illuminator (such as a fourth illuminator, in a non-limiting example) in the green wavelengths may be included to alternately illuminate the brain for reflectance measurements. The emission light is routed to a complementary metal oxide semiconductor (CMOS) image sensor (APTINA Inc.) through a bi-convex collection lens (Edmund Optics Inc.) and an emission filter. The CMOS sensor may be wire bonded to a custom motherboard (Sierra Circuits), consisting of a powering module for the LED illuminator and field programmable gate array (FPGA) circuits for data acquisition programming. In a non-limiting example, the scope may have a total weight of 4 g and height of 2.3 cm, both comparable to head-mounted graded refractive-index (GRIN) lens microscopes. The mesoscope may provide uniform illumination of the whole cortex and may incorporate mating features that allow the mesoscopes to be quickly mounted and dismounted from the mice.

In one configuration, the mesoscope incorporates a single LED for illumination. In other configurations, three filtered LED light sources may be provided to illuminate the two hemispheres more uniformly and with greater illumination of lateral section of the cortex than the single LED configuration. A additional unfiltered green or red LED may provide illumination for reflectance measurements. Illumination may be optimized by using benchtop testing, in vivo implantation and testing, or simulations, such as ZEEMAX simulations, which may be performed to iteratively optimize the illumination. The incorporation of additional LEDs may marginally increase the weight of the device by 0.21 g, which can be offset by some of the configurations described below.

Weight may be considered when configuring a device. The overall weight of the device may be configured to be less than a specified amount of the bodyweight of a subject. In a non-limiting example, a threshold weight may be established as approximately 15% of the bodyweight of a mouse (<4.0 g) to permit free behavior and mobility.

Additional electronic components may be included on the PCB board for in situ amplification of ECoG signals. To reduce the weight of the device, the optical path length can be reduced by using shorter focal length collection lenses. This will allow reduction in the overall length of the device housing, with an estimated 0.6 g reduction in weight. CAD designs may be combined with optical simulations (ZEEMAX) for the opto-mechanical design process, and scripts may be run for virtually aligning and positioning optical elements in a 3D CAD model to obtain the best focal distance. Eliminating the need for focusing mechanisms may further reduce the weight of the housing.

3D printing of the housing may allow for rapid design changes; e.g., adding LEDs, changing the orientation of LED illumination, changing the relative distance between optical components, and the like. However, using conventional 3D printers may limit the housing wall thickness to being greater than 0.5 mm because of minimum feature sizes of the 3D printer as well as mechanical properties of the polymer. Once the relative dimensions of the optical component have been optimized, a system such as a CNC machine may be used to mill the housing frame out of aluminum. With such a system, wall thicknesses of less than 0.2 mm can be achieved and this may allow for ~0.7 g reduction in overall weight.

Mounting the mesoscope to the subject may be performed in a manner that avoids introducing stress to the subject prior to behavioral testing. In some configurations, magnets such as rare earth magnets may be incorporated in the bottom surface of the imaging housing, with corresponding metallic inserts in the implanted polymer skull to provide for ease of mounting and dismounting the system to the subject. In some configurations, kinematic mating features on the inner vertical face of the housing may mate with a corresponding feature attached to the polymer skull. This provides for the head-mounted scope to be precisely attached to the implanted headplate. Thus, micrometer scale positioning can be achieved quickly and repeatedly.

In some configurations, isolation and shielding may be used to reduce noise of the Mesoscope. Offsetting any additional weight from these features may be obtained by incorporating optical filters that are custom-coated on 0.2 mm thick glass (Semrock Inc.) as compared to 2 mm thick glass filters. Motion artifacts may be induced by collision of the camera with walls of the behavior arena. The mating feature of the mesoscope to the subject may be optimized to make the connection robust and also the behavioral arena may be configured to limit or eliminate collisions.

In some configurations, the transparent polymer skulls may include ECoG electrode arrays. The film, such as a PET film, that may be used to provide a robust and transparent protective barrier for the brain in the polymer skulls may also be used as a substrate for printed electronics. In a non-limiting example, a 32-channel ECoG array may be fabricated on the PET film prior to integration into the transparent polymer skull.

The ECoG array may be created using an inkjet-printing system or a 3D printing system, and the like. Flexible ECoG sensor arrays may be fabricated by 3D printing electrodes and traces onto thin, such as 50 μm thick, transparent PET substrate. A plurality of channels may be used with the array, such as a 6-channel version, an 18-channel array, or any other number of channels. In one non-limiting example of a 6-channel array, the exposed sensing electrode diameter is 300 μm, the trace width and spacing are 150 μm each, and the total thickness of the printed silver is a few 100 nm. The electrodes and traces may be printed using a commercially available high-conductivity silver nanoparticle ink (Silverjet DGP 40LT-15C, ANP) because it can be sintered to achieve excellent conductivity at low temperatures that will not damage the PET substrates. After sintering, the conductive traces may be encapsulated with a biocompatible insulating coating (parylene-C), while the sensing electrodes and contact pads may be left exposed.

ECoG arrays may be optimized to be compatible with pan-cortical imaging, where a large fraction of the sensing array may be selected to be transparent. The diameter of the electrodes and the width of the traces may be selected to be 100 μm and 75 μm, respectively to provide for pan-cortical imaging. Optimizing an oxygen plasma treatment of the PET surface prior to printing may be performed, which causes the printed features to be 'pinned' and limits the spreading of the ink.

A multilayer inkjet-printing scheme may be used to significantly reduce the footprint of the wiring by routing the traces on top of each other. In a non-limiting example, each printed silver layer may be electrically insulated by inkjet-printing PMMA56 over the traces, leaving electrodes exposed. The electrodes may be distributed evenly across the cortex, but the placement of the electrodes and traces can be quickly modified for different experiments. After all layers are printed, the entire array may be encapsulated with 5 μm of parylene-C, which is an excellent biocompatible moisture barrier and electrical insulator.

The silver electrodes may be coated with biocompatible conducting polymer to facilitate chronic implantation, such as with poly(3,4-ethylenedioxythiophene) polystyrene sulfonate (PEDOT:PSS, Sigma Aldrich), which has been shown to be stable across chronic implantation.

In some configurations, benchtop testing of printed ECoG arrays may be performed. The sheet resistance of the printed features may be characterized using 4-point resistivity measurements (Keysight B1500A analyzer). Permeability of the encapsulation layer over the conductive traces may be tested by submerging the arrays in saline and measuring the resistance to a reference electrode. This test may be repeated following sterilization with a cold sterilant (Metricide, Metrex Inc.) to ensure that the encapsulation properties are not degraded. The electrode-electrolyte interface may be characterized using electrochemical impedance spectroscopy (EIS) (Gamry potentiostat) and analyzed with a software such as MATLAB. Different surface coatings (e.g., conductive polymers, gold, Ag/AgCl) that alter the electrode capacitance and surface roughness may be investigated to minimize the charge-transfer resistance of electrodes, if necessary. To determine the long-term viability of the electrode materials after implantation, encapsulation and EIS may be measured following prolonged submersion in phosphate buffered saline (PBS). Photoelectric artifacts may be tested by illuminating the device using broad wavelength LEDs and measuring the subsequent noise voltage with a high-precision device parameter analyzer (Keysight B1500A).

The printed ECoG arrays may be interfaced with a digital electrophysiology system to analyze the neural signals. The printed electrodes on the PET may be connected to a small custom interface board using anisotropic conductive film (ACF) and a hot-bar bonding tool (Ohashi Co. Ltd.). The ACF bond may be more compact and robust for chronic implantation. A common surface-mount connector (Omnetics Connector Corp) may be installed onto the interface board, and the board-to-PET interface may be strain-relieved using epoxy. The ECoG sensor array may be connected to a RHD2132 headstage (32 unipolar input channels, Intan Technologies) to amplify, filter, and digitize the signals. A serial peripheral interface (SPI) cable may connect the headstage to an interface circuit board (Intan Technologies) that may link the headstage to a computer, where the signals may be analyzed in a software, such as MATLAB.

In some configurations, integration of a printed ECoG may be made with the 3D-printed cranial prosthesis. Printed ECoG arrays may cut to the shape and bonded onto the 3D-printed PMMA frame. A laser cutter (Speedy 400 Flex, Trotec Inc.) may provide a 20 μm resolution when cutting the PET. The PET film may then be manually aligned to the PMMA frame using a custom-fabricated alignment jig and glued into place using quick-setting epoxy adhesive (Scotch-Weld, 3M Inc.).

In some configurations, a head-mounted scope may be used. Given the flexibility of the electronic circuits described above, they can be easily flexed upwards to interface with an amplifier headstage that may be integrated into the head-mounted microscope. Once the ECoG electrode arrays have been fully characterized, the mesoscope may incorporate an RHD2132 amplifier chip and a mating Omnetics connector, in one non-limiting example.

The neural computations underlying free and unrestrained behaviors are distributed across the cerebral cortical network. To monitor this, the temporal-spatial patterns of cerebral cortical Ca2+ and ECoG activity of a subject's behavior may be monitored, such as in: exploration of an empty arena; exposure to and habituation to the arena with two novel objects; and removal of the objects and return to the empty arena. Introduction of a novel object may be made without change of location. In other situations, changing location of one of the objects without changing the object may be performed.

In some configurations a head-mounted camera allows for changes in GCaMP6f fluorescence to be sampled. To minimize motion artifacts, images may be co-registered with a reference image using image registering functions. The imaged cerebral cortex may be functionally segmented using independent components analysis (ICA) of the co-registered images. Upon visual inspection, the components associated with tissue movements may be eliminated from further analysis. The components describing neural activity may be cataloged across trials based on spatial correlations. Repeated imaging of several subjects may demonstrate the presence of consistent independent components (ICs).

Time courses may be defined for each cerebral module, and a plurality of time courses may be defined for each module. The time series determined by the average intensity of all pixels in the component of interest may provide the modulation pattern. Applying ICA for the pixels in the component of interest, the independent activity features present in the modulation pattern may be extracted. To quantify the directional interactions between cerebral modules conditional Granger causality between time courses may be used. The strength of causal interaction with other time courses may be determined. The direction and magnitude between a pair of time courses of interest may be determined by the difference between the interaction strength of the pair and the interaction strength of the reciprocal pair. To establish the temporal relationships of the directional interactions the time course of interest may be shifted, such as in 20 ms steps, to cover a time interval of ±1.5 s, and repeat the analysis at each step.

Magnitude and phase of the spatial coherence of activity may be used to characterize the spatio-temporal patterns in the fluorescence based on space-frequency singular value decomposition (SVD). The Fourier transform of the fluorescence intensity time series of pixels may determine the dominant frequency, corresponding to the highest spectral power. The leading spatial mode of the space-frequency SVD of the dominant frequency Fourier coefficient may determine the phase gradient across all pixels covering the cerebral cortex that may characterize evolution of activation patterns within each trial.

In some configurations, the ECoG recordings may be undertaken simultaneously with the optical recordings. In a non-limiting example, 32 channels may be sampled at 20 kHz. The analysis may focus on the $\alpha$ (8-12 Hz), $\beta$ (12-32 Hz), low $\gamma$ (35-42 Hz) and high $\gamma$ (45-100 Hz) bands that underlie numerous aspects of the cerebral role in sensorimotor and cognitive processes. For each behavior state, the average power in each frequency band of interest may be evaluated across all the locations of the ECoG electrodes, as well as the coherence of each frequency band across all pairs of electrodes. The Granger analysis in the frequency domain may allow to investigate the directional interactions within the frequency bands at the recording locations. A measure for the state of arousal may also be determined using the $\alpha$-band activity of the ECoG recordings.

The systems and methods of the present disclosure may provide for important monitoring of cerebral cortical activity and behavior in the freely moving subject. The patterns of neuronal Ca2+ and ECoG activity across the dorsal cerebral cortex and how these spatial-temporal patterns reflect different behavioral classes may be determined. How these patterns change with novelty, defined both by object or location may be determined. Information and solutions to implementing simultaneous optical and ECoG recordings in freely moving subjects may be provided. The patterns of Ca2+ and ECoG may change not only during exploration of the arena but also during rest. The changes in patterning will include changes in the ICs, Granger interactions among regions, phase-gradients as well as ECoG frequency bands and coherence between ICs.

Figure 4:
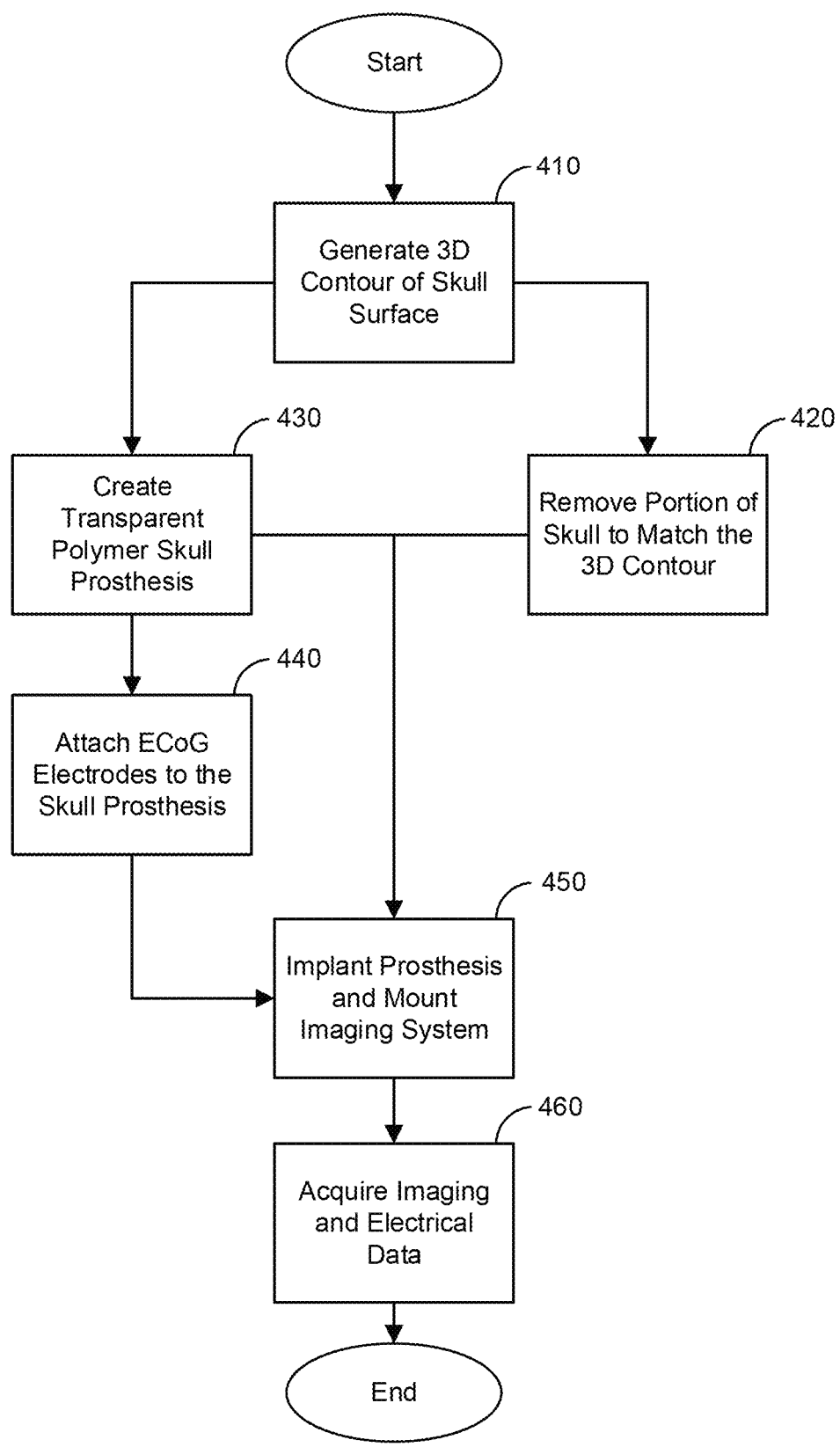
FIG. 4 depicts non-limiting example steps for imaging and recording electrical data of a subject in accordance with the present disclosure.

Referring to FIG. 4, non-limiting example steps for imaging and recording electrical data of a subject according to the present disclosure are shown. A 3D contour of a skull of a subject is generated at step 410. A portion of the subject's skull may be removed at step 420 to match the generated contour. A transparent polymer skull prosthesis may be created at step 430. An ECoG array or other electrodes may be attached to the prosthesis at step 440. The prosthesis may be implanted in a subject and an imaging system such as the mesoscope described herein be attached at step 450. Imaging and electrical data may then be acquired or monitored at step 460.

Figure 5A:
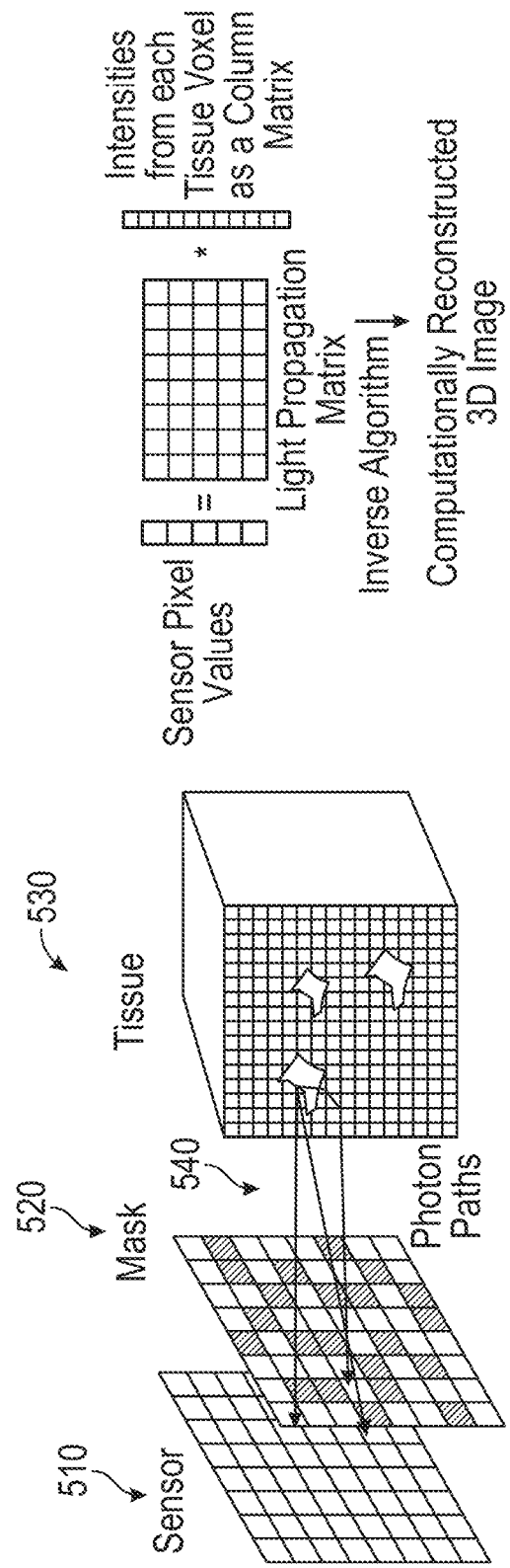
FIG. 5A depicts an architecture for a non-limiting example miniaturized light-field imaging module (MLIM) that may be used in accordance with the present disclosure.

Referring to FIG. 5A, an architecture for a non-limiting example of a miniaturized light-field imaging module that may be used in accordance with the present disclosure is shown. To enable fast volumetric imaging, a lensless miniaturized light-field imaging module (MLIM) may be embedded within the cranial prostheses described above. The overall architecture includes a CMOS sensor 510 covered by an imaging mask 520, which blocks 50% of the light 540 entering the sensor in a quasi-random fashion. A second layer of microLEDs with a filter mask for delivered filtered light to the tissue 530 being illuminated may be diced and bonded on top of the masked CMOS sensor 510.

The image formed at the sensor may be a combination of the tissue anatomy and location of individual cells and the mask pattern, which together capture both the positions, and angular orientations of the incident photons. The intensity of light from a source as a function of position and angle is known as a light field, and this knowledge allows its location in all three dimensions to be determined using computational imaging techniques. These techniques may employ an image reconstruction algorithm, which may utilize prior/post-hoc anatomical knowledge of the tissue to constrain the possible solutions to the correct set of neuronal signals. This process may apportion all detected photons to neural sources, addressing the problem of out-of-focus light in software—unlike confocal or multiphoton systems that avoid out-of-focus light by the design of their hardware. This allows the sensor to capture information from the full 3D volume—thereby eliminating the issue of out of focus light—a major issue faced by traditional epi-fluorescence and confocal imaging modalities and allows the MLIM to achieve single cell resolution from 3D tissue volumes. Since there are no moving parts, and 2D snapshots can be gathered at very high speeds (>150 Hz using commercially available CMOS sensors).

The patterned mask may cause the fluorescence emitted from each voxel in 3-D space to project a unique pattern of light onto the image sensor. The image recorded by the sensor is the incoherent superposition of all the patterns from all voxels emitting fluorescent light. To reconstruct the fluorescent power of each source, this superposition may be decomposed into those unique patterns. This decomposition can be represented as a linear algebra problem. This pattern is determined by the mask, light transport properties of brain tissue, and properties of the image sensor. If the intensity of each pixel of the sensor into a column vector Y, the fluorescent power of each voxel as a column vector X, and the pattern on the sensor from each voxel as columns of a matrix A. X is the quantity to be determined, Y is the measured data, and A is determined from knowledge of the mask and optical properties of brain tissue. The equation becomes $Y=AX$. Rather than solve for every voxel in the space, knowledge of nucleus locations may be used to solve only for each nucleus. This reduced form of the equation may generally be over-constrained because the number of cells, and thus number of elements of the unknown is much smaller than the number of pixels, which is the number of knowns in the column vector Y. The MLIM, and its reconstruction algorithm, may achieve single-cell, single-spike resolution for thousands of cells per MLIM.

In a non-limiting example, the sensor may be able to record neuronal activities from the whole cerebral cortex simultaneously via volumetrically sampling a total lateral area of 7 mm² area of surface of the cortex. The microfabricated geometry of the device may allow for a miniaturized physical scale that will allow deployment in freely behaving mice. Multiple neural interfacing approaches may be used with the sensor, including microfluidic channels and photonic waveguides for simultaneous pharmacological and/or optogenetic interventions respectively. In some configurations, the sensor may include 3D printed electrodes, 3D printed microfluidic channels, 3D printed photonic waveguides, 3D printed transistors, 3D printed sensors, 3D printed tomography devices, 3D printed controllers, and the like. A sensor may also be configured to measure neurotransmitter concentrations, and/or blood oxygenation levels.

Figure 5B:
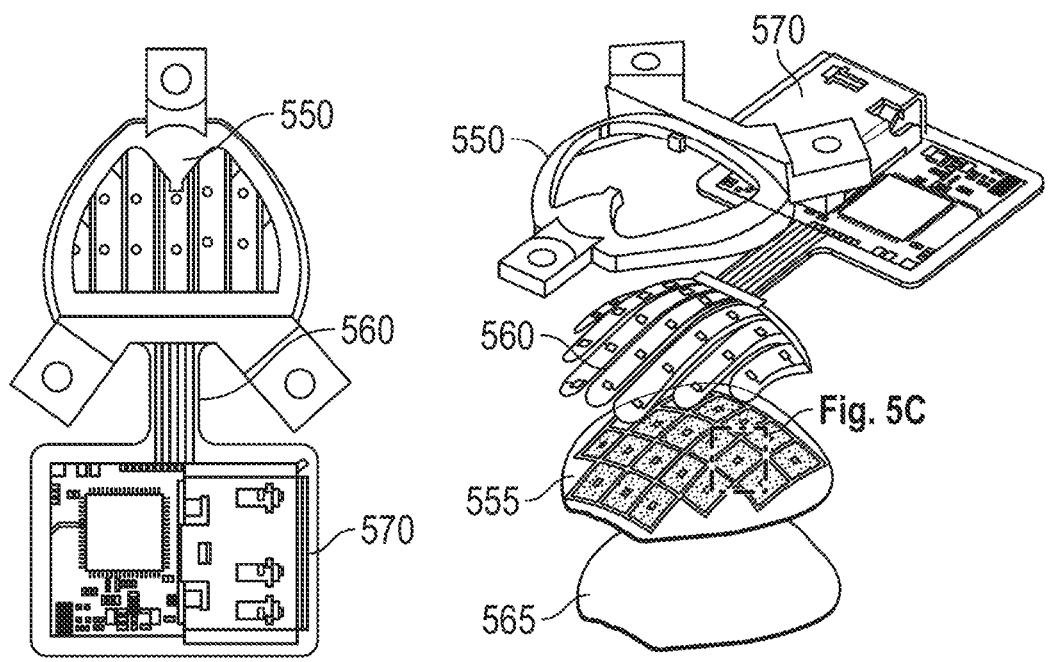
FIG. 5B is a profile view of a non-limiting example MLIM device of FIG. 5A.
Figure 5C:
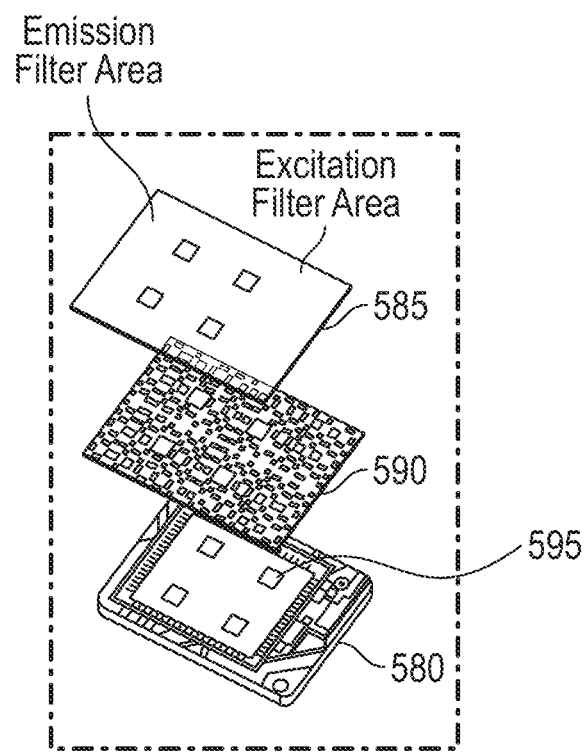
FIG. 5C is an exploded view of a non-limiting example MLIM array sensor element of the non-limiting example MLIM device of FIG. 5B.

Referring to FIGS. 5B and 5C, a non-limiting example MLIM of FIG. 5A is shown. A 3D printed frame 550 may provide support for a MLIM array 555, an MLIM interface cable 560, and a PET film 565. The frame 550 may include provisions for a computer datalink 570. A miniature CMOS image sensor 580 integrated with emission filter and a quasi-random photomask 590 may be included with the MLIM. In a non-limiting example, the total lateral dimensions of the CMOS sensor 580 with packaging may be only 750 µm×750 µm. The CMOS sensors 580 may be retrofitted with the image mask optical filter layer sheet 585. An LED illuminator 595 may be integrated between the masked CMOS sensor 580 and the filter layer 585. This may allow tissue underneath the MLIM sensor to be illuminated directly by the MLIM Referring to FIG. 5C, an exploded view of a non-limiting example MLIM array sensor element is shown. The MLIM array may be configured to cover the whole dorsal cortex, or a substantial portion of the dorsal cortex. A "tortoise shell" replacement skull prosthesis may include interspersed arrays of micro LED's and CMOS sensors equipped with integrated photomasks. In one example, the array may allow imaging up to 500,000 neurons from the surface of the mouse cortex during free behavior.

Small Animal Imaging Example

In a non-limiting small animal example, over 1,800 neurons in 16 randomly accessed planes were imaged with fields of views of 350 µm×350 µm. Based on previous estimates, the transparent headplates allowed access to over 25,000 neurons using single-photon imaging and over 800,000 neurons via 2P imaging across the whole dorsal cortex. The flexibility of 3D CAD design and 3D printing allow the prosthetic devices to be easily modified to incorporate a range of additional functionalities including the ECoG electrode arrays.

Miniature light-field imaging scopes weighing up to 4 g were successfully implanted in freely moving mice and were shown to not impede open field behavior. Preliminary experiments (n=6 mice) in a 30 cm×30 cm open field arena indicate mice readily acclimatize to the device within 5-6 training sessions lasting 15-30 minutes. No appreciable difference in total distance moved and mean velocity was observed between mice acclimatized to the head-mounted scope as compared to naïve mice. Mice with mesoscopes perform a range of behavior including climbing on arena walls. The device can current image a field of view of 8 mm×11 mm clearly discriminating 100 µm wide printed lines separated by 500 µm. The mesoscope thereby allows sub-millimeter resolution imaging across the whole field of view, sufficient for mesoscale mapping for cortical activity dynamics. Ca2+ dynamics were imaged in Thy1-GCaMP6f mice during free behavior in the open field arena.

Surgical implantation of polymer skulls: Thy1-GCaMP6f mice were given anti-inflammatory agents to prevent cortical stress and analgesics, anesthetized with 1-2% isoflurane in pure oxygen and affixed in the stereotax. Standard aseptic procedures were followed throughout the surgery. After incising the scalp, the skull surface was cleaned using a microcurette. The neurosurgery robot automatically milled the desired craniotomy as described earlier in section B.1 (FIG. 2), followed by covering with gel foam soaked in sterile cortex buffer 22 to keep tissue moist. The sterilized polymer skulls were placed on the skull for replacement. Tissue glue (Vetbond, 3M) was applied to the suture lines and at the points at which the polymer skulls sat flush on the skull. Skull screws were implanted to stabilize the implant before application of dental cement. Mice recovered from anesthesia and returned to their home cages following standard post-operative procedures. Behavioral training, or imaging through the polymer skulls was done once the mice fully recovered from the surgery.

Behavioral testing of head-mounted cameras: Mice were acclimatized to the head-mounted mesoscopes. For initial validation, the mean velocity of the mouse was measured with and without the mesoscopes to quantify their effect on behavior and develop a guideline for the range of behaviors that can be performed. A thresholding algorithm distinguished between periods of quiescence and active locomotion. Ca2+ imaging was performed from Thy1-GCaMP6f transgenic mice (#024275 Jackson Labs). The raw data acquired up to 50 Hz, was preprocessed in ImageJ52 and custom MATLAB scripts. Each frame was spatially binned to reduce file size. After pre-processing, the videos were converted to ΔF/F format, which is the percentage change in fluorescent intensity over the baseline value. The ΔF/F time series was extracted from major sensorimotor areas using region of interest (ROI) analysis. Ca2+ activity was determined by generating a time series of the ΔF/F at candidate brain regions. Synchrony between different brain regions was assessed and reported on how different behavioral states changed these relations. Macroscopic anatomical landmarks such as blood vessels were used to quantify lateral motion artifact and correct for them algorithmically.

Inkjet-printed ECoG sensor arrays on PET with up to 18 channels using the fabrication procedure outlined above were used on the mice. The ECoG array is capable of recording local field potentials (LFPs) in a head-fixed anesthetized mouse. The array was connected to a digital electrophysiology system (RHD 2164, Intan Technologies) through an FFC connector using a custom-made daughterboard. A ~4 mm×4 mm craniotomy was performed on the left hemisphere exposing the somatosensory cortex of a C57Bl/6J mouse. The 6-channel ECoG array was then placed onto the cortical surface and covered with agarose gel made with conductive saline. LFPs were recorded at each site and analyzed in MATLAB, where the power spectra were calculated using a fast Fourier transform (FFT). Consistent with previous reports, we observed the general suppression of signal power as well as typical 'burst suppression' activity in the anesthetized state with qualitative differences seen in the ECoG recordings when mice were awake.

In vivo testing: Mice were implanted with the new implants using the same procedure described above. After the initial post-operative recovery duration (3 days) electrode impedance spectra and baseline signal recordings were performed three times a week. The EIS was carried out using the Gamry impedance meter on a low-current setting. The neural signals from the ECoG arrays was amplified in situ using a 32-channel headstage (RHD2000, Intan Technologies) which was connected to a computer via a USB interface board. LFPs were acquired at each of the recordings sites, and the power spectra were analyzed for each electrode using fast-Fourier transform and segregated at physiologically relevant frequency bands. For each electrode in each session, the mean power in each band across the chronic implantation period was calculated. These experiments were repeated during experiments where mice were freely moving with the head-mounted mesoscope as described above. The overall stability of the electrode impedances were monitored during chronic implantation and different electrode coating materials were iteratively explored to achieve stable long term implantation. Comprehensive histological analyses of the brain tissue was performed looking at microglia counts and astrocyte activation.

Behavioral task: All behavioral and recording sessions lasted 10 min and occurred in the dark-phase of the daily cycle in a behavioral arena (30×30 cm×30 cm). During the inter-session interval (5 min), mice were placed back in their home cage and the arena walls and objects wiped with 90% EtOH. The arena was placed on a new paper sheet before each session. On the first day, all mice started with ten recording sessions during the initial exposure to the empty arena. On the second day, mice were exposed to five empty sessions, followed by five sessions in which two identical objects were firmly positioned in the arena (Initial Condition). For the next two days, the mice were re-exposed to the Initial Condition configuration during ten recording sessions. On the test day, the mice were separated into three experimental groups. All groups started with two Initial Condition sessions. For the next sessions, the first group was exposed to the empty arena, the second group was exposed to a novel object, and the third group was exposed to a familiar object in a novel location. All mice were rotated through the different five days recording sequences for at least two times, separated by one week each.

Behavioral recordings and analysis: Six high-speed, high resolution cameras (DMK 33UP1300, The Imaging Source) monitored the behavior of each animal throughout all recording sessions. Three cameras, recording at 50 frames/s, covered the entire arena in the x, y, and z directions. Three more cameras, oriented in the z direction above the arena, were placed directly above each of the three possible object locations and focused on recording whisking (200 frames/s). For behavioral analysis, the arena was partitioned into 25 equal bins. Data was binned based on the nose position. Exploratory behavior of the objects were determined by the head direction pointing to the object at a distance of less than 2 cm. Occupancy maps, based on the time a mouse inhabited a given arena bin, provided a behavioral measure of novelty for each session. Motions of the various body parts, including, head, nose, paws, and whiskers, were extracted from the high-speed, high-resolution cameras and tracked using image segmentation and feature matching MATLAB algorithms. The 3D motion of each body segment was reconstructed using 3D Tracker an open-source software from Open Ephys (www.openephys.org). Mouse behaviors were classified using a combination of supervised (Convolutional Neural Networks) and unsupervised (Expectation-Maximization) learning algorithms. The behavioral data was correlated with the corresponding Ca2+ imaging and ECoG data.

mTBI Example Application mTBI induces both short and long duration changes in cerebral cortical dynamics and neuronal morphology, resulting in neuronal circuit dysfunction and behavioral abnormalities. One configuration of the present disclosure provides for real-time imaging of the activity and morphology of single neurons and neural population dynamics in the awake, behaving subject. The ability to image the cerebral cortex over a large field-of-view (FOV) at multiple scales for months and simultaneously monitor behavior provides an advantage of the present disclosure. The results of such monitoring provide an unprecedented assessment of how the cerebral cortex responds to mTBI across spatial, temporal, physiological, and anatomical dimensions.

The effects of mTBI may be evaluated on the activity of cerebral cortical neurons and neuronal population dynamics, both across the entire cortical surface (mesoscopic) and at the cellular level. The morphological effects of mTBI in the cerebral cortex may be evaluated over time, such as by monitoring changes in dendritic spines and neuronal processes.

Use of robotic principles and 3D printed optically clear and morphologically conformant cranial prostheses provides imaging access to most of the dorsal cerebral cortex in transgenic mice expressing a fast Ca2+ indicator (GCaMP6f) in neurons. Changes in Ca2+ fluorescence reflect the activity and spiking of single neurons. Mesoscopic imaging of Ca2+ signals provides for a real-time assessment of how neuronal networks throughout the dorsal cerebral cortex respond to mTBI, such as to mTBI induced by controlled cortical impact (CCI). In the same subjects on alternate days, two-photon (2P) imaging may be used to determine how CCI disrupts the activity of single neurons. Simultaneous with the Ca2+ imaging, computer algorithms and high-speed video imaging track multiple aspects of behavior including treadmill walking, whisking, and grooming. Longitudinal mesoscopic and 2P Ca2+ imaging may be performed over a period of time, such as a 4 month period (1 month before and then 3 months following mTBI) and correlated with the behavioral recordings. Behavior may also be monitored simultaneously and compared to the structural changes following single and repeated mTBI.

In one non-limiting example, two cohorts of mice were studied, one subjected to a single mTBI event and the second subjected to repeated mTBI events. mTBI results in widespread and persistent changes in neuronal activity dynamics. The experimental design combines mesoscopic and cellular level Ca2+ imaging in awake mice with high speed assessment of the animal's behavior before and following CCI. Transgenic mice expressing a fast Ca2+ indicator (Thy1-GCaMP6f) were used in the non-limiting example.

Replacement of cranium with transparent windows: To track functional and morphological changes in the brain post-CCI, a robotic surgery platform was used to generate an accurate 3D contour map of the skull and perform precise craniotomies followed by replacement with transparent windows matching the cranial geometry. The cranial windows were an optically clear polymer (PET) mounted on a 3D printed acrylic frame with a titanium head plate for structural stability and head fixation to a custom treadmill. The cranial windows remained optically transparent and functional for up to 7 months. Histological analyses indicate little or no inflammatory response to the implants. The flexibility of the CAD design and 3D printing, allows to easily incorporate additional functionalities into the windows, for example recording electrodes or microfluidic channels.

Controlled cortical impact (CCI): a modified version of CCI that emulates mTBI was used. Using a precision cortical impactor (PCI3000, Hatteras Instruments), a rounded silicon tip (tip diameter 3 mm) impacted the brain at a slow speed (0.43 m/s) to a depth of 1.5 mm, greatly decreasing the likelihood of hemorrhaging, which does not occur in mTBI. Mice were initially implanted with a brain window containing a 4 mm round opening in the PET film centered over the motor cortex, with a second removable PET film overlaid on top to seal the opening and protect the brain. Following recovery from surgery, mesoscopic and 2P imaging was performed for 1 month to establish the baseline in each animal. Next, mice were divided into two cohorts (10 mice per cohort). Anesthetized with isoflurane, the first cohort received a single CCI, and the second cohort received a single CCI per day for 3 days to simulate repetitive mTBI. The cranial windows provided the ability to image within minutes to hours following injury (a period where little is known), for up to 3 months in the same animal.

Neuronal GCaMP6f Ca2+ imaging with CCI: Both mesoscopic and 2P imaging were performed 2 times per week for 3 months to monitor how the disruptions of neuronal activity progressed following single and repetitive mTBI. For both types of imaging, an awake mouse was head-fixed on a custom disk treadmill, and allowed to walk freely during imaging. Mesoscopic single-photon fluorescence imaging was performed using a high-speed imaging system mounted on a macroscope (Nikon AZ-100) with a 1× objective, resulting in a FOV of most of the dorsal cortical surface with a final pixel size of ~35×35 µm. An imaging trial was acquired at 50 Hz for 2 minutes (2400 frames), and 10 trials obtained in a session.

Brain windows were implanted on Thy1-GCaMP6f mice (n=12) expressing the Ca2+ indicator GCaMP6f in Layer II/III and Layer V pyramidal neurons. Mesoscopic Ca2+ imaging of the dorsal cerebral cortex showed the widespread and dynamic nature of neuronal activity in a control mouse on the treadmill. During an imaging trial, different regions of the cerebral cortex were active at various times indicated by large increases and decreases in GCaMP6f fluorescence levels. In this example, motor cortical (14 s), retrosplenial (80 s), and somatosensory (90 s) regions were highly modulated at different times during a trial with a strong tendency for homotopic cortical regions to be active bilaterally. These complex spatial and temporal patterns were highly repeatable across days and animals.

Analysis of the mesoscopic Ca2+ imaging quantified how CCI changes the cerebral cortical activity patterns. After normalizing the images to the mean fluorescence (ΔF/F), to quantify the activity patterns independent component analysis (ICA) was performed on the image sequence during each trial, segmenting the cortical surface into functionally distinct cortical domains called independent components (ICs). ICA is entirely data driven, without any prior assumptions and is widely used to define functionally correlated domains in resting state fMRI. The number, spatial organization and strength of the ICs change was assessed with mTBI. Also, the time course of each IC, defined as the time series of average ΔF/F, was correlated with the behavioral data and the time courses of the other ICs to determine directional correlations using Granger Causality Analysis (GCA). GCA quantified how each IC related to behavior and to the rest of the cerebral cortex network and how mTBI disrupted these cortical networks and cortical-behavioral relationships. Statistical significance of the effects was rigorously evaluated using bootstrapping, a common, powerful, distribution free method of hypothesis testing.

Alternating with the mesoscopic imaging, 2P Ca2+ imaging (Leica SPSII TCS) was done in the same animals using a 25× (0.95 NA) water immersion objective, resulting in a FOV of ~350×350 µm. An imaging trial was acquired at 50 Hz for 2 minutes (2400 frames), and 10 trials obtained in a session. 2P imaging with these cranial windows allowed sampling the activities of individual neurons in different locations out of an estimated 1.1 million cells across the entire dorsal cortex.

After correcting for xy motion artifacts (Fiji, NIH), regions of interest (ROIs) were placed over every cell identified in the FOV and their activity defined by ΔF/F time series. The xyz coordinates of each imaging session were used to register the position of single neurons, allowing for longitudinal imaging of the same neurons before and after mTBI. To assess changes in single cell activity with mTBI, the number, frequency, and amplitude of the Ca2+ transients were determined. GCA was used to determine local connectivity among cells and the relations between cell activity and behavior and how these change after mTBI.

Behavioral assessment: Two high-speed IR sensitive cameras (DMK 33UP1300, The Imaging Source) recorded the mice behavior throughout the mesoscopic and 2P imaging sessions under diffuse IR light that did not interfere with the Ca2+ imaging. Limb and oral facial movements were monitored at 50 Hz and whisking at 200 Hz. Treadmill sensors measured angular displacements at 200 Hz. A machine learning algorithm was trained to detect and monitor movement and automatically classify animal behavior into distinct categories including rest, walking, grooming, sniffing, and whisking. The algorithm generated time series of movements defining these behaviors that were correlated with both the mesoscopic and 2P activity. In the Behavioral Phenotyping Core, mice were tested weekly on rotarod, beam walk and grip strength to obtain several standard measures of behavior before and after mTBI.

Following CCI, large alteration in neuronal Ca2+ signals at both the mesoscale and cellular scale at the site of impact and surrounding regions were expected. Graded changes in other regions were also expected. These alterations changed the baseline ICs, network and cellular dynamics and their correlations with behavior.

Short and long-term changes to neuronal morphology following single and repeated mTBI was evaluated. Mice expressing YFP in cortical neurons (Thy1-YFP) were implanted with the brain windows, divided into two cohorts (10 mice each) subjected to the CCI paradigms, with behavioral assessments performed as described above.

Neuronal YFP imaging: The brain windows also allowed multi-scale high-resolution structural imaging in the same animal before and after mTBI. A brain window implanted on a Thy1-YFP mouse expressing YFP in Layers II/III and Layer V pyramidal neurons of the cortex enabled imaging of fine structural elements of cortical circuits spread across the dorsal cerebral cortex. Pyramidal cell bodies were imaged up to 600 μm deep in the cortex. Whole cortical columns can be imaged over large contiguous volumes of tissue. Throughout the FOV, different regions can be targeted for high resolution structural imaging of individual neurons and their dendrites. At high resolution, sub-cellular structures including dendrites, dendritic processes, and spines can be resolved.

Dendritic spine density and morphology measurements following mTBI: Spine turnover is a common phenomenon is cortical circuits that is quantified by tagging spines that are lost as well as gained over multiple imaging sessions. The xyz coordinates of several ROIs spanning the injured hemisphere and contralateral hemisphere were recorded for longitudinal imaging of the same dendritic regions following single or repeated mTBI. Dendritic spine density was measured in Layer II/III by counting the number of spines spanning a 10 μm section of the dendrite. Density measurements were divided up into three different morphological shapes of spines: mushroom, stubby, and filopodia. Dendritic beading is also a common occurrence following dendrite injury, and was also measured in the same 10 μm sections. Additionally, a rostral-caudal and medial-lateral axis was imaged in each mouse over time to monitor the progression of neuronal structural changes in the injured hemisphere spanning the core, penumbra, and healthy tissue.

Following CCI, a large decrease in the YFP fluorescence at both the mesoscale and cellular scale at the center of the injured tissue was expected. Decreased dendritic spine density, increased dendritic beading and increased axonal injury was expected in the injured tissue. The extent to which these changes evolved in time correlated with the behavioral measures after CCI.

Multi-scale and multi-modality imaging tools were used to investigate the effects of mTBI in the mouse brain over time. By using both mesoscopic and 2P imaging of neuronal Ca2+ activity in the awake animal, changes resulting from CCI were determined at both the global and single cell levels. By imaging chronically over months, the effects of the initial insult(s) on neuronal activity were determined and how the acute changes in neuronal functioning and morphology with mTBI evolved into secondary effects. When combined with the simultaneous imaging and rigorous quantification of behavior, the changes in neuronal activity were linked directly to behavioral outcome. Using the same approach for the 2P morphological imaging following CCI provided a powerful structure-function-behavior assessment of the effects of mTBI in the cerebral cortex. A test platform for new therapeutics may be based upon the methods using the model to monitor blood flow or specific neuronal populations (e.g. neuroglia, inhibitory versus excitatory neurons) and testing specific cognitive behaviors in relation to the multi-scale imaging.

Motor Cortex Mapping Example in Primates

Complex behaviors like motor control, perception or cognition require the dynamic recruitment and contribution of large populations of neurons distributed over different regions of the brain. Therefore, a mechanistic understanding of the neural processes underpinning brain function requires the capability to probe and manipulate large populations of neurons over time intervals ranging from hundreds of milliseconds to months. Optical imaging and stimulation may be used to asses these complex functions according to the present disclosure. Disease models may also be used in combination with the imaging and stimulation systems for understanding neurological and psychiatric disorders and developing new therapies.

The systems and methods of the present disclosure may allow the investigation of both the spatial and the temporal properties of the functional organization of the motor cortices in behaving monkeys. The optical cranial prostheses and a head-mounted microscope may be used for wide FOV cellular resolution imaging in the cerebral cortex of monkeys to assess the spatio-temporal responses of neurons in the dorsal motor cortex (PMd) and primary motor cortex (MI). Large population studies in different cortical areas may be used to study the interactions between functionally different areas of the cerebral cortex. The ease of customization may encourage multiple neural interfacing approaches, including microfluidic channels and photonic waveguides for simultaneous pharmacological and/or optogenetic interventions.

Brain windows in the monkey may be used and CT scans and MRIs of the monkey's head may be obtained. The 3D skull image may be aligned with the primate brain atlas in Cicerone to define the implantation site and annotate the scan image. This may be imported to VGstudio Max (Volume Graphics Inc.) to generate point clouds in the inner and outer skull surfaces at the implant location. The point cloud can imported into a CAD software, such as SolidWorks, Dassault Systems Inc., to generate the surface, anchor and artificial dura of the personalized brain window.

Figure 6:
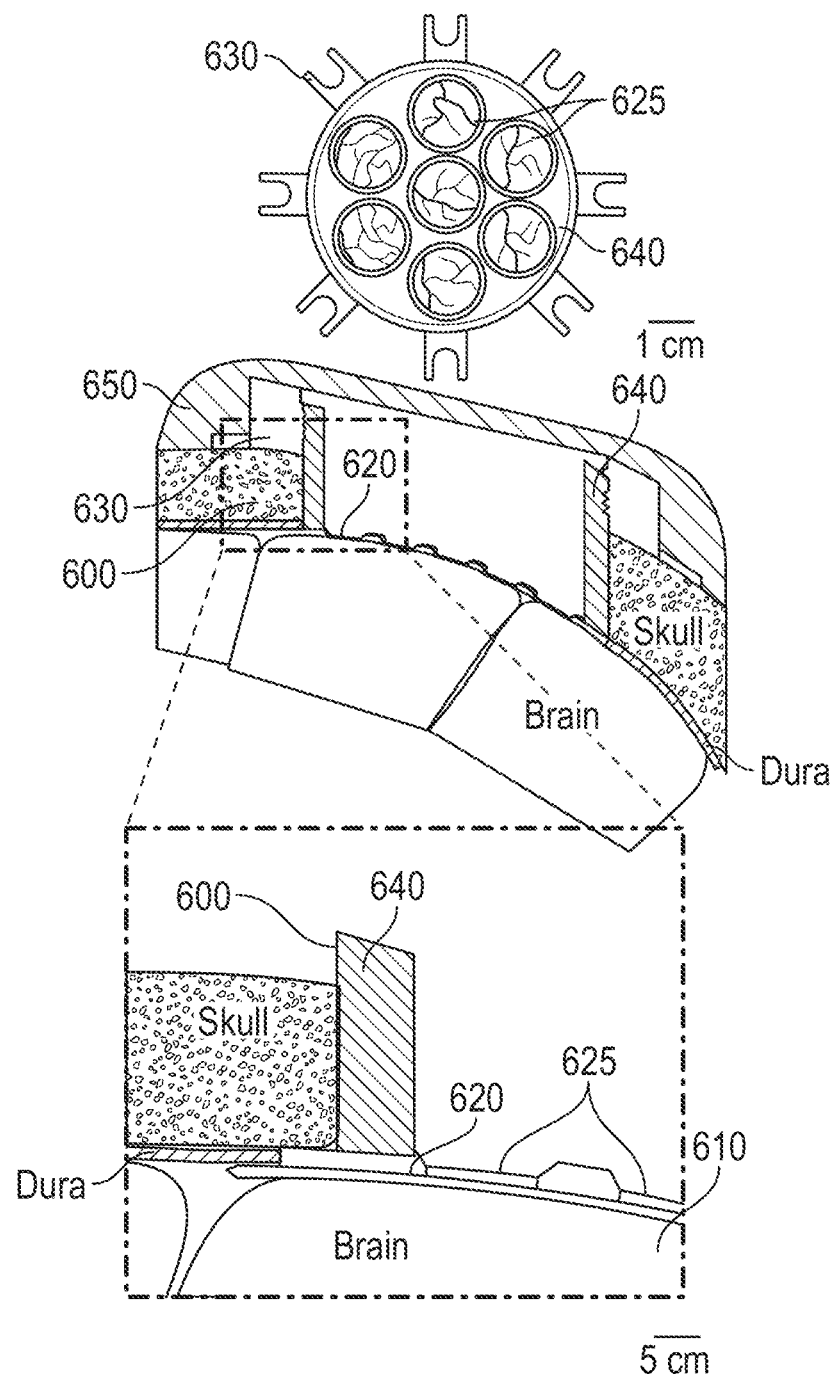
FIG. 6 is a profile view of an interface between a transparent skull prosthesis and a subject's tissue surface where an artificial dura may be used.

Referring to FIG. 6, a profile view of an interface between a transparent skull prosthesis 600 and a subject's tissue surface 610 is shown where an artificial dura 620 may be used. In some configurations, the artificial dura 620 may be similar to that used for intrinsic optical imaging and optogenetic stimulation in the monkey. A 2 cm diameter brain window 625 may be implanted over the PMd and MI, with up to seven 6 mm diameter imaging windows. The outer ring 630 may act as an anchor to the skull and conform to perimeter of the craniotomy. A rigid inner ring 640, conforming to the native skull, may fit inside the outer ring 630 and slide axially with respect to the brain surface. Circular holes, such as holes of 6 mm in diameter with 200 μm thick glass coverslips, may be embedded in the inner ring. The rigid structural design may mitigate brain motion, with the optical windows allowing imaging access through the glass coverslips. The structural elements of the non-human primate (NHP) brain windows may be fabricated using a system such as a 4-axes CNC mill. The brain window design may accommodate the imaging module. An ergonomic cap 650 may be fabricated to protect and hermetically seal the window when not in use.

Figure 7:
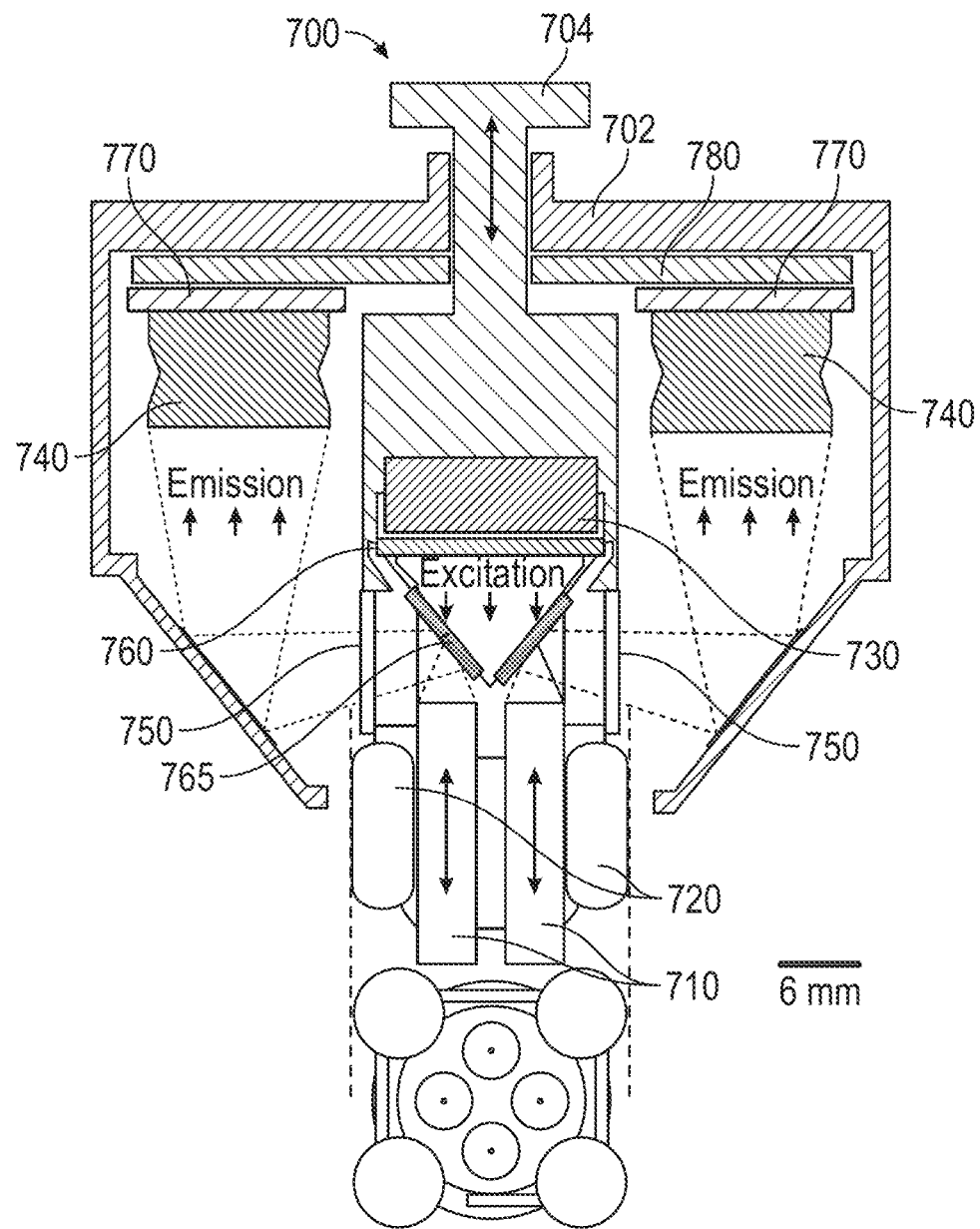
FIG. 7 is a cross section for a non-limiting example head-mounted microscope that may be used in accordance with the present disclosure.

Referring to FIG. 7, a cross section for a non-limiting example head-mounted microscope 700 is shown. The head-mountable microscope may include main housing 702, adjustable tissue illumination housing 704, and be capable of imaging single neurons across, and may mount within the brain window. The head-mounted microscope includes an array of GRIN lenses 710, such as 4 GRIN lenses as shown (N.A. of 0.45, GRINtech GMBH), each independently imaging FOVs separated by a select pitch, such as 1.5 mm diameter FOVs separated by 2 mm pitch. Axial position of each GRIN lens may be adjusted by a miniature Microdrive 720, part of an inner specimen illumination module moving with coarse resolution within main housing. The illumination module may include a LED light source 730 with a parabolic focusing lens, and an excitation filter 750 to illuminate the brain region underneath the GRIN lenses 710 via a filter 760, such as a cube edge filter coated with dichroic film 765. Emission light captured by the GRIN lenses 710 may be reflected off of the dichroic cube edge, and may be imaged into a camera, such as a CMOS sensors 770, fitted with a focusing lens 740 capable of tuning focal length from 25-35 mm. The focus mechanisms may be adapted from off-the-shelf smart phone camera modules with effective focal length of 28-35 mm, while using higher quantum yield, CMOS sensors 770 used for other in vivo imaging applications for the sensing element. A motherboard 780 may interface with the CMOS sensors, control sensor focusing lenses 740, and microdrives 720 positioning the GRIN lenses 710. It may also have an FPGA circuit programmed for data acquisition, and a wireless module for remote control and data acquisition.

In a non-limiting example, the camera array may operate at a frame rate of 15 Hz—fast enough to capture Ca2+ signals. A GRIN lens may have an effective FOV of 1.5 mm×0.8 mm, thus allowing simultaneous imaging across 4.8 mm$^2$ of the primate cortex. The pixel size of the CMOS sensor may have an effective magnification of the 4.1-5.2×.

The miniature microscope may be mounted directly on the implanted brain window and laterally adjusted using an x-y stage to position the microscope on top of one of the imaging windows. Each GRIN lenses may be independently lowered to the imaging window using its dedicated microdrive and the focus module may be used to focus the image acquired by the corresponding CMOS sensor. Images will be acquired while the monkey is performing the behavioral task. The raw data may be pre-processed to reduce file size and correct for motion artifacts. Automated cell identification and segmentation may be performed. Principle component analysis (PCA) may be used to reduce the dimensionality of the imaging data by removing the components that contain noise information. This may be followed by independent component analysis (ICA) to identify the spatial and temporal properties of visualized cells by segmenting the data into statistically independent spatial and temporal signals. This combined PCAICA approach is stochastic and may over estimate the number of cells in a given frame. Thus, the analyses may be done across multiple frames and may manually select only those cells that appear repeatedly across frames. The Ca2+ imaging described above may be performed over different windows in different recording sessions, thereby increasing the extent of PMd and MI evaluated.

Non-Limiting Example of Imaging Glutamate Release Dynamics

A Mesoscope in accordance with the present disclosure may be used to measure dynamic changes in extracellular glutamate release in the cortex during transition from wakefulness to natural sleep. Glutamate is an important neurotransmitter that regulates neural activity and cerebral metabolism during wakefulness and sleep. However, much of the previous work studying extracellular release has been done using fixed-potential amperometry, or optical imaging in head-fixed mice. Inducing sleep in head-fixed mice is challenging and typically requires sleep deprivation which can alter the overall sleep structure and patterns of rapid eye-movement (REM) and non-REM (NREM) sleep.

In a non-limiting example, the transparent prostheses in accordance with the present disclosure allowed for local field potential (LFP) recording electrodes to be incorporated in the dorsal hippocampus in Emx-CaMKII-Ai85 mice, expressing iGluSnFR in glutamatergic neocortical neurons. Mice were allowed to naturally transition to sleep in their home cage. Glutamate activity across the whole dorsal cortex during wakefulness, REM sleep and NREM sleep was acquired. Hippocampal LFP clearly indicated transition to NREM sleep and subsequently REM sleep. Spontaneous cortical activity patterns during quiet wakefulness and NREM were highly synchronized across hemispheres[4]. In addition, cortical activity patterns were not necessarily global changes in activity state and were instead composed of complex local activity patterns. The transition from wakefulness to NREM sleep and REM sleep resulted in decreased fluorescence, indicated reduced cortical glutamate activity. A reduction of slow cortical glutamate fluctuations during REM sleep also occurred. Correlation analysis of cortical activity revealed that connectivity decreases in REM sleep compared to quiet wakefulness and NREM sleep. The strength of functional connectivity is less in NREM sleep compared to quiet wakefulness. The transition from REM sleep to wakefulness included increased glutamate activity across the cortex.

Raw data of spontaneous glutamate activity was preprocessed based on: First, the time series of each pixel was filtered using a zero-phase bandpass Chebyshev filter between 0.1 and 5 Hz. Then a baseline signal was calculated by averaging all the frames, and the fluorescence changes were quantified as DF/F×100, where F is the filtered signal. To reduce spatial noise, images were filtered by a Gaussian kernel (5×5 pixels, sigma=1).

State scoring: Behavioral states were scored visually using hippocampal LFP and movement signal in 10 s epochs. Movement signals were calculated. Active wakefulness (aW) was characterized by theta hippocampal activity and high movements. Quiet wakefulness (qW) was characterized by theta hippocampal activity and minimum movement. NREM sleep (N) was characterized by large irregular activity in hippocampus and no movement. REM sleep (R) was characterized by theta hippocampal activity and no movement.

Correlation analysis: A uniform meshgrid with ~1.2 mm distance between its points was laid on the field of view and signal at each ROI (0.2 mm$^2$) was calculated. Quiet wake, NREM sleep and REM sleep were scored for each recording based on above criteria and Pearson correlation coefficients were calculated between each ROIs during qW, NREM and REM. For comparison, correlation matrices were averaged across all ROIs The present disclosure has described one or more preferred embodiments, and it should be appreciated that many equivalents, alternatives, variations, and modifications, aside from those expressly stated, are possible and within the scope of the invention.

What is claimed is:

1. A system for acquiring data from a tissue of a subject, comprising:
 a computer system configured to:
  access images of at least one of bone or connective tissue adjacent to a surface of the tissue of the subject, and
  generate a contour of the at least one of bone or connective tissue;
 a prosthesis to conform to and replace the contour of the at least one of bone or connective tissue, and to replace a missing section of the bone or connective tissue; and
 an imaging system, in communication with the computer system affixed to the prosthesis for acquiring data of the tissue of the subject,
 wherein the imaging system comprises a sensor,
 wherein a plurality of electrodes is attached to the prosthesis,
 wherein a combination of the plurality of electrodes and the prosthesis is optically transparent, and
 wherein the imaging system includes at least one of a single photon microscope, a miniaturized fluorescence imaging device, a 2-photon (2P) microscope, or a miniaturized light-field imaging module (MLIM).

2. The system of claim 1, wherein the imaging system includes a light source for illuminating the tissue integrated within the imaging system.

3. The system of claim 1, further comprising at least one of a second sensor, a waveguide, or a microfluidic channel coupled to the prosthesis and configured to acquire data of the tissue of the subject.

4. The system of claim 3, wherein the at least one sensor, electrode, waveguide, or microfluidic channel is at least one of 3D printed, inkjet printed, aerosol deposited, or screen printed.

5. The system of claim 3, wherein the sensor is configured to measure at least one of neurotransmitter concentrations or blood oxygenation levels.

6. The system of claim 3, wherein the plurality of electrodes are in an array.

7. The system of claim 6, wherein the array is an electrocorticography (ECoG) array.

8. The system of claim 7, wherein conductive traces of the ECoG array are encapsulated with a biocompatible insulating coating, while sensing electrodes are left exposed.

9. The system of claim 8, wherein the computer system is further configured to determine the biocompatible insulating coating by determining stability of electrode impedances with different electrode coating materials.

10. The system of claim 3, wherein the at least one sensor is inkjet printed, and wherein the at least one sensor is a multilayer inkjet-printed sensor electrically insulated by an insulating layer that is inkjet printed over traces of the at least one sensor.

11. The system of claim 1, wherein the prosthesis is 3D printed.

12. The system of claim 1, wherein the prosthesis is a biocompatible polymer film.

13. The system of claim 12, wherein the biocompatible polymer film is polyethylene terephthalate (PET) film.

14. The system of claim 1, wherein the acquired data includes at least one of optical reporters of intracellular calcium, membrane voltage, images captured at the resolution of sub-cellular structures within a cell, or release of neuromodulators.

15. The system of claim 1, wherein a weight of the imaging system is less than approximately 15% of a bodyweight of the subject.

16. The system of claim 1, wherein the plurality of electrodes is at least one of integrated with the prosthetic or printed onto the prosthetic.

17. A system for acquiring data from a tissue of a subject, comprising:
 a computer system configured to:
  access images of at least one of bone or connective tissue adjacent to a surface of the tissue of the subject, and
  generate a contour of the at least one of bone or connective tissue;
 a prosthesis to conform to and replace the contour of the at least one of bone or connective tissue, and to replace a missing section of the bone or connective tissue; and
 an imaging system, in communication with the computer system affixed to the prosthesis for acquiring data of the tissue of the subject,
 wherein the imaging system comprises a sensor,
 wherein a plurality of electrodes is attached to the prosthesis,
 wherein a combination of the plurality of electrodes and the prosthesis is optically transparent, and
 wherein the imaging system includes at least one of a single photon microscope, a miniaturized fluorescence imaging device, a 2-photon (2P) microscope, or a miniaturized light-field imaging module (MLIM).

18. The method of claim 17, wherein the prosthesis is optically transparent.

19. The method of claim 18, further comprising illuminating the tissue with a light source integrated within the imaging system.

20. The method of claim 17, further comprising acquiring data of the tissue of the subject using at least one of a second sensor, an electrode, a waveguide, or a microfluidic channel coupled to the prosthesis.

21. The method of claim 20, wherein the at least one sensor, electrode, waveguide, or microfluidic channel is at least one of 3D printed, inkjet printed, aerosol deposited, or screen printed.

22. The method of claim 21, further comprising configuring the sensor to measure at least one of neurotransmitter concentrations or blood oxygenation levels.

23. The method of claim 20, wherein the prosthesis includes a plurality of electrodes in an array.

24. The method of claim 23, wherein the array is an electrocorticography (ECoG) array fabricated thereon.

25. The method of claim 24, wherein conductive traces of the ECoG array are encapsulated with a biocompatible insulating, while sensing electrodes are left exposed.

26. The method of claim 25, further comprising determining the biocompatible insulating coating by determining stability of electrode impedances with different electrode coating materials.

27. The method of claim 20, wherein the at least one sensor is inkjet printed, and wherein the at least one sensor is a multilayer inkjet-printed sensor electrically insulated by an insulating layer that is inkjet printed over traces of the at least one sensor.

28. The method of claim 17, wherein the prosthesis is 3D printed.

29. The method of claim 17, wherein the prosthesis is a biocompatible polymer film.

30. The method of claim 29, wherein the biocompatible polymer film is polyethylene terephthalate (PET) film.

31. The method of claim 17, wherein the acquired data includes at least one of optical reporters of intracellular calcium, membrane voltage, images captured at the resolution of sub-cellular structures within a cell, or release of neuromodulators.

32. The method of claim 17, wherein the imaging system is removably affixed to the prosthesis.

33. The system of claim 17, wherein the plurality of electrodes is at least one of integrated with the prosthetic or printed onto the prosthetic, and wherein the plurality of electrodes follow the contour of the prosthetic.

* * * * *